US 8,808,245 B2

(12) United States Patent
Taylor et al.

(10) Patent No.: US 8,808,245 B2
(45) Date of Patent: Aug. 19, 2014

(54) POWERED IRRIGATOR FOR SINUS CAVITY RINSE WITH DETACHABLE RESERVOIR

(75) Inventors: Kurt M. Taylor, Fort Collins, CO (US); Gary L. Sokol, Longmont, CO (US); Kenneth A. Hair, Fort Collins, CO (US); Harold A. Luettgen, Windsor, CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 13/545,764

(22) Filed: Jul. 10, 2012

(65) Prior Publication Data

US 2012/0277677 A1    Nov. 1, 2012

Related U.S. Application Data

(63) Continuation of application No. 12/970,345, filed on Dec. 16, 2010, which is a continuation-in-part of application No. 29/352,098, filed on Dec. 16, 2009, now Pat. No. Des. 629,884, which is a continuation-in-part of application No. 29/364,670, filed on Jun. 25, 2010, now Pat. No. Des. 676,126.

(60) Provisional application No. 61/287,026, filed on Dec. 16, 2009, provisional application No. 61/287,100, filed on Dec. 16, 2009, provisional application No. 61/369,378, filed on Jul. 30, 2010.

(51) Int. Cl.
*A61M 1/00*      (2006.01)
*A61J 7/00*      (2006.01)

(52) U.S. Cl.
USPC ................. 604/151; 604/27; 604/77

(58) Field of Classification Search
USPC ............... 604/27, 30, 35, 36–43, 77, 79, 131, 604/151; 601/162; 222/383.1; 433/80, 89
See application file for complete search history.

(56) References Cited

U.S. PATENT DOCUMENTS 465,559 A    12/1891    Good
555,588 A    3/1896     Spencer
(Continued)

FOREIGN PATENT DOCUMENTS

CA    851479    9/1970
CH    655237    4/1987
(Continued)

OTHER PUBLICATIONS

US Re. 27,274, 01/1972, Mattingly (withdrawn).
(Continued)

*Primary Examiner* — Matthew F Desanto
(74) *Attorney, Agent, or Firm* — Dorsey & Whitney LLP

(57) ABSTRACT

A powered irrigator for use in rinsing nasal cavities including a main body having a handle and fluid reservoir detachably coupled to one another, an outlet nozzle extending from a top end of the handle, a pump mechanism operably coupled to a power source, and a switch operably coupled to the power source for turning the pump mechanism on and off, and when the switch turns on the pump mechanism, fluid flows from the fluid reservoir into a first fluid coupling between the reservoir and the pump mechanism and into a second fluid coupling between the pump mechanism to the outlet nozzle. The reservoir includes a generally centrically body defining a cavity and at least two tabs connected to the cylindrical body and extending inwards therefrom. The at least two tabs operably connect the reservoir to the handle portion to releasably secure the reservoir to the handle portion.

13 Claims, 19 Drawing Sheets

(56) References Cited

U.S. PATENT DOCUMENTS

| | | |
|---|---|---|
| 1,278,225 A | 9/1918 | Schamberg |
| 1,464,419 A | 8/1923 | Gill |
| 1,498,267 A | 6/1924 | Hachman |
| 1,650,686 A | 11/1927 | Binks |
| 1,681,320 A | 8/1928 | Bergl et al. |
| 1,933,454 A | 10/1933 | Sidney |
| 2,107,686 A | 2/1938 | Bramsen et al. |
| 2,115,959 A | 5/1938 | Lewis |
| 2,230,238 A | 2/1941 | Duberstein et al. |
| 2,417,759 A | 3/1947 | Johnson |
| 2,571,921 A | 10/1951 | Morris |
| 2,578,864 A | 12/1951 | Tupper |
| D169,996 S | 7/1953 | Vuillement |
| 2,669,233 A | 2/1954 | Friend |
| 2,794,437 A | 6/1954 | Tash |
| 2,722,458 A | 11/1955 | Wahlin |
| 2,783,919 A | 3/1957 | Ansell |
| 2,811,283 A | 10/1957 | Bowen |
| 2,984,452 A | 5/1961 | Hooper |
| 2,987,261 A | 6/1961 | McCuiston et al. |
| 3,089,490 A | 5/1963 | Goldberg |
| 3,096,913 A | 7/1963 | Jousson |
| 3,144,867 A | 8/1964 | Trupp et al. |
| 3,176,883 A | 4/1965 | Davis, Jr. |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,204 S | 11/1967 | St. Clair et al. |
| D209,395 S | 11/1967 | Gilbert |
| 3,363,808 A | 1/1968 | Gorman |
| 3,370,214 A | 2/1968 | Aymar |
| 3,391,696 A | 7/1968 | Woodward |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,455,294 A | 7/1969 | Adler et al. |
| 3,465,751 A | 9/1969 | Powers |
| 3,487,828 A | 1/1970 | Troy |
| 3,489,268 A | 1/1970 | Meierhoefer |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| 3,572,375 A | 3/1971 | Rosenberg |
| 3,578,884 A | 5/1971 | Jacobson |
| 3,583,609 A | 6/1971 | Oppenheimer |
| 3,590,813 A | 7/1971 | Roszyk |
| 3,608,548 A | 9/1971 | Lewis |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,977 A | 5/1974 | Balamuth et al. |
| 3,820,532 A | 6/1974 | Eberhardt et al. |
| 3,827,147 A | 8/1974 | Condon |
| 3,840,795 A | 10/1974 | Roszyk et al. |
| 3,847,145 A | 11/1974 | Grossan |
| 3,854,209 A | 12/1974 | Franklin et al. |
| 3,874,506 A | 4/1975 | Hill et al. |
| 3,881,868 A | 5/1975 | Duke |
| 3,898,739 A | 8/1975 | Gayso |
| 3,912,125 A | 10/1975 | Acklin |
| 3,943,628 A | 3/1976 | Kronman et al. |
| 3,973,558 A | 8/1976 | Stouffer et al. |
| 4,001,526 A | 1/1977 | Olson |
| 4,004,302 A | 1/1977 | Hori |
| 4,007,739 A | 2/1977 | Bron et al. |
| D246,667 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,083,840 A | 4/1978 | Schoefberger |
| 4,108,167 A | 8/1978 | Hickman et al. |
| 4,108,178 A | 8/1978 | Betush |
| 4,109,650 A | 8/1978 | Peclard |
| D250,546 S | 12/1978 | Pick et al. |
| D250,601 S | 12/1978 | Pick et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,179,051 A | 12/1979 | Thomas |
| 4,182,038 A | 1/1980 | Fleer |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| 4,248,589 A | 2/1981 | Lewis |
| 4,249,899 A | 2/1981 | Davis |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,356,941 A | 11/1982 | McRoskey et al. |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| D271,028 S | 10/1983 | Adams |
| 4,410,110 A | 10/1983 | Del Bon et al. |
| 4,412,823 A | 11/1983 | Sakai et al. |
| 4,432,496 A | 2/1984 | Ito |
| 4,439,206 A | 3/1984 | Hildebrand et al. |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,489,535 A | 12/1984 | Veltman |
| 4,512,769 A | 4/1985 | Kozam et al. |
| 4,513,891 A | 4/1985 | Hain et al. |
| 4,517,962 A | 5/1985 | Heckele |
| 4,526,797 A | 7/1985 | Stone, Jr. |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,555,469 A | 11/1985 | Erdmann et al. |
| D283,374 S | 4/1986 | Cheuk-Yiu |

(56) References Cited

U.S. PATENT DOCUMENTS

| | | |
|---|---|---|
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,612 A | 10/1986 | Weber et al. |
| 4,629,425 A | 12/1986 | Detsch |
| 4,636,198 A | 1/1987 | Stade |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,760,937 A | 8/1988 | Evezich |
| 4,770,632 A | 9/1988 | Ryder et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,828,149 A | 5/1989 | Hester |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| D305,262 S | 12/1989 | Nichols |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,128 A | 5/1990 | Brody |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| D314,702 S | 2/1991 | Gonzalez |
| 4,989,590 A | 2/1991 | Baum et al. |
| 4,998,880 A | 3/1991 | Nerli |
| 5,013,241 A | 5/1991 | von Gutfeld et al. |
| 5,014,884 A | 5/1991 | Wunsch |
| 5,019,054 A | 5/1991 | Clement et al. |
| D317,940 S | 7/1991 | Brenner |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kandler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,062,795 A | 11/1991 | Woog |
| 5,064,168 A | 11/1991 | Raines et al. |
| D322,314 S | 12/1991 | Ohbayashi |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,110,051 A | 5/1992 | Bennett |
| 5,125,543 A | 6/1992 | Rohrabacher et al. |
| 5,125,835 A | 6/1992 | Young |
| 5,127,553 A | 7/1992 | Weinstein |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,183,186 A | 2/1993 | Delaney, Jr. |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,297,962 A | 3/1994 | O'Connor et al. |
| D346,212 S | 4/1994 | Hosl |
| 5,301,846 A | 4/1994 | Schmitz |
| 5,302,123 A | 4/1994 | Bechard |
| 5,316,054 A | 5/1994 | Hall et al. |
| 5,317,691 A | 5/1994 | Traeger |
| 5,321,865 A | 6/1994 | Kaeser |
| 5,328,099 A | 7/1994 | Petit et al. |
| 5,330,634 A | 7/1994 | Wong et al. |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,354,849 A | 10/1994 | Schoefberger |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,468,148 A | 11/1995 | Ricks |
| 5,470,305 A | 11/1995 | Arnett et al. |

(56) References Cited

U.S. PATENT DOCUMENTS

| | | |
|---|---|---|
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,193 A | 4/1996 | Ballini et al. |
| 5,505,916 A | 4/1996 | Berry, Jr. |
| D369,656 S | 5/1996 | Vos |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,025 A | 9/1996 | Kinsel |
| 5,556,001 A | 9/1996 | Weissman et al. |
| 5,564,629 A | 10/1996 | Weissman et al. |
| 5,570,966 A | 11/1996 | Phelan |
| D377,091 S | 12/1996 | Scott, Sr. |
| 5,611,376 A | 3/1997 | Chuang |
| 5,616,028 A | 4/1997 | Hafele et al. |
| 5,622,501 A | 4/1997 | Levy |
| 5,634,791 A | 6/1997 | Matsuura et al. |
| 5,636,987 A | 6/1997 | Serfaty |
| 5,640,735 A | 6/1997 | Manning |
| 5,649,530 A | 7/1997 | Ballini |
| 5,653,591 A | 8/1997 | Loge |
| 5,655,686 A | 8/1997 | Jermyn |
| 5,659,995 A | 8/1997 | Hoffman |
| 5,667,483 A | 9/1997 | Santos |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| 5,709,545 A | 1/1998 | Johnston et al. |
| D390,744 S | 2/1998 | Otero |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,654 A | 7/1998 | Foley et al. |
| 5,795,153 A | 8/1998 | Rechmann |
| 5,806,723 A | 9/1998 | DuBose |
| 5,833,065 A | 11/1998 | Burgess |
| 5,836,030 A | 11/1998 | Hazeu et al. |
| 5,851,079 A | 12/1998 | Horstman et al. |
| D403,511 S | 1/1999 | Serbinski |
| D405,525 S | 2/1999 | Barrett et al. |
| D406,334 S | 3/1999 | Rosenthal et al. |
| 5,876,201 A | 3/1999 | Wilson et al. |
| D408,511 S | 4/1999 | Allen et al. |
| 5,897,872 A | 4/1999 | Picciano |
| 5,899,878 A | 5/1999 | Glassman |
| 5,901,397 A | 5/1999 | Hafele et al. |
| 5,934,902 A | 8/1999 | Abahusayn |
| D413,975 S | 9/1999 | Maeda |
| 5,967,377 A | 10/1999 | Glynn |
| D417,082 S | 11/1999 | Classen et al. |
| 5,993,402 A | 11/1999 | Sauer et al. |
| 6,006,952 A | 12/1999 | Lucas |
| 6,030,215 A | 2/2000 | Ellion et al. |
| 6,035,769 A | 3/2000 | Nomura et al. |
| 6,039,180 A | 3/2000 | Grant |
| D424,197 S | 5/2000 | Sydlowski et al. |
| D425,615 S | 5/2000 | Bachman et al. |
| D425,981 S | 5/2000 | Bachman et al. |
| 6,056,548 A | 5/2000 | Neuberger et al. |
| 6,056,710 A | 5/2000 | Bachman et al. |
| D426,300 S | 6/2000 | Conforti |
| D426,633 S | 6/2000 | Bachman et al. |
| 6,089,865 A | 7/2000 | Edgar |
| 6,124,699 A | 9/2000 | Suzuki et al. |
| 6,135,358 A | 10/2000 | Ballini |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| 6,193,512 B1 | 2/2001 | Wallace |
| 6,193,932 B1 | 2/2001 | Wu et al. |
| 6,199,239 B1 | 3/2001 | Dickerson |
| D439,781 S | 4/2001 | Spore |
| 6,217,835 B1 | 4/2001 | Riley et al. |
| D441,861 S | 5/2001 | Hafliger |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,238,377 B1 | 5/2001 | Liu |
| 6,241,705 B1 | 6/2001 | Ko-Wen |
| 6,247,929 B1 | 6/2001 | Bachman et al. |
| D448,236 S | 9/2001 | Murray |
| 6,293,436 B2 | 9/2001 | Faughnder et al. |
| 6,293,792 B1 | 9/2001 | Hanson |
| D449,884 S | 10/2001 | Tobin et al. |
| 6,343,174 B1 | 1/2002 | Neuberger |
| D453,453 S | 2/2002 | Lun |
| 6,363,565 B1 | 4/2002 | Paffrath |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,572 B2 | 12/2002 | Hood et al. |
| 6,502,584 B1 | 1/2003 | Fordham |
| D470,660 S | 2/2003 | Schaber |
| 6,520,384 B2 | 2/2003 | Mehta |
| 6,540,718 B1 | 4/2003 | Wennek |
| 6,558,344 B2 | 5/2003 | McKinnon et al. |
| 6,561,808 B2 | 5/2003 | Neuberger |
| D475,346 S | 6/2003 | McCurrach et al. |
| 6,589,477 B1 | 7/2003 | Frieze et al. |
| 6,602,071 B1 | 8/2003 | Shultz et al. |
| 6,632,091 B1 | 10/2003 | Cise et al. |
| D481,794 S | 11/2003 | Krinsky |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,663,386 B1 | 12/2003 | Moelsgaard |
| 6,669,059 B2 | 12/2003 | Mehta |
| D486,066 S | 2/2004 | Hannen et al. |
| D486,573 S | 2/2004 | Callaghan et al. |
| 6,688,497 B2 | 2/2004 | Mehta |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,736,792 B1 | 5/2004 | Liu |
| 6,739,782 B1 | 5/2004 | Rehkemper et al. |
| 6,740,053 B2 | 5/2004 | Kaplowitz |
| D490,896 S | 6/2004 | Bogazzi |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D493,888 S | 8/2004 | Reschke |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| D495,954 S | 9/2004 | Solomon |
| 6,796,796 B2 | 9/2004 | Segal |
| D497,107 S | 10/2004 | Hama et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,907,879 B2 | 6/2005 | Drinan et al. |
| D509,585 S | 9/2005 | Kling et al. |
| 6,976,669 B2 | 12/2005 | Van Zijll Langhout et al. |
| D513,638 S | 1/2006 | Pan |

(56) References Cited

U.S. PATENT DOCUMENTS

| | | |
|---|---|---|
| 7,080,980 B2 | 7/2006 | Klupt |
| D529,661 S | 10/2006 | Schmidt |
| D530,010 S | 10/2006 | Luettgen et al. |
| D530,815 S | 10/2006 | Murphy et al. |
| 7,117,555 B2 | 10/2006 | Fattori et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| 7,276,035 B2 | 10/2007 | Lu |
| 7,306,121 B2 | 12/2007 | Ophardt et al. |
| D558,509 S | 1/2008 | Bodum et al. |
| D558,510 S | 1/2008 | Bodum et al. |
| 7,314,456 B2 | 1/2008 | Shaw |
| D562,404 S | 2/2008 | Jansen et al. |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D584,151 S | 1/2009 | Murphy |
| 7,500,584 B2 | 3/2009 | Schutz |
| D590,492 S | 4/2009 | Powell |
| D590,493 S | 4/2009 | Harlan et al. |
| D595,136 S | 6/2009 | Canamasas Puigbo |
| D601,697 S | 10/2009 | Sobeich et al. |
| D603,708 S | 11/2009 | Handy |
| D608,645 S | 1/2010 | Handy et al. |
| D612,736 S | 3/2010 | Pecora |
| 7,670,141 B2 | 3/2010 | Thomas et al. |
| 7,677,888 B1 | 3/2010 | Halm |
| D613,550 S | 4/2010 | Picozza et al. |
| D613,601 S | 4/2010 | Yoneda |
| 7,703,696 B2 | 4/2010 | Eddins et al. |
| D621,949 S | 8/2010 | Seki et al. |
| 7,814,585 B1 | 10/2010 | Reich |
| D627,458 S | 11/2010 | Bisson et al. |
| D629,884 S | 12/2010 | Stephens |
| D630,314 S | 1/2011 | Stephens |
| 7,862,536 B2 | 1/2011 | Chen et al. |
| 7,878,403 B2 | 2/2011 | Hennick et al. |
| D634,213 S | 3/2011 | Thompson |
| D634,630 S | 3/2011 | Taylor |
| D634,631 S | 3/2011 | Taylor |
| 7,959,597 B2 | 6/2011 | Baker et al. |
| D640,872 S | 7/2011 | Nanda |
| 7,971,761 B1 | 7/2011 | Kudlu |
| D653,953 S | 2/2012 | Wakeman |
| 8,113,832 B2 | 2/2012 | Snyder et al. |
| 8,486,029 B2 | 7/2013 | Cacka et al. |
| 2002/0158089 A1 | 10/2002 | Mehta |
| 2003/0062367 A1 | 4/2003 | Robinson et al. |
| 2003/0098249 A1 | 5/2003 | Rollock |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0209222 A1 | 10/2004 | Snyder et al. |
| 2005/0049620 A1 | 3/2005 | Chang |
| 2005/0101894 A1 | 5/2005 | Hippensteel |
| 2005/0271531 A1 | 12/2005 | Brown et al. |
| 2006/0008373 A1 | 1/2006 | Schutz |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0253087 A1 | 11/2006 | Vlodaver et al. |
| 2007/0082316 A1 | 4/2007 | Zhadanov et al. |
| 2007/0105065 A1* | 5/2007 | Snyder et al. .................... 604/77 |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0008979 A1 | 1/2008 | Thomas et al. |
| 2008/0294124 A1 | 11/2008 | Mehta |
| 2009/0070949 A1 | 3/2009 | Sagel et al. |
| 2009/0082706 A1 | 3/2009 | Shaw |
| 2009/0124945 A1 | 5/2009 | Reich et al. |
| 2009/0163839 A1 | 6/2009 | Alexander |
| 2009/0234325 A1 | 9/2009 | Rozenberg et al. |
| 2009/0281454 A1 | 11/2009 | Baker et al. |
| 2010/0015566 A1 | 1/2010 | Shaw |
| 2010/0152653 A1 | 6/2010 | Hoke et al. |
| 2010/0190132 A1 | 7/2010 | Taylor |
| 2010/0209870 A1 | 8/2010 | Thomas et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0266980 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0084099 A1 | 4/2011 | Carta |
| 2011/0097683 A1 | 4/2011 | Boyd et al. |
| 2011/0139149 A1 | 6/2011 | Cacka et al. |
| 2011/0139824 A1 | 6/2011 | Cacka et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0319840 A1 | 12/2011 | Hair |
| 2012/0021374 A1 | 1/2012 | Cacka et al. |
| 2012/0045730 A1 | 2/2012 | Sayder et al. |
| 2012/0077145 A1 | 3/2012 | Tsurukawa |
| 2012/0141952 A1 | 6/2012 | Snyder et al. |
| 2012/0295220 A1 | 11/2012 | Thomas et al. |

FOREIGN PATENT DOCUMENTS

| | | |
|---|---|---|
| DE | 1466963 | 5/1969 |
| DE | 2409752 | 9/1975 |
| DE | 2545936 | 4/1977 |
| DE | 2910982 | 2/1980 |
| DE | 29602605 | 4/1996 |
| EP | 0023672 | 7/1980 |
| FR | 2556954 | 6/1985 |
| FR | 2654627 | 5/1991 |
| GB | 881807 | 10/1958 |
| GB | 1182031 | 2/1970 |
| GB | 2018605 | 10/1979 |
| JP | 2-134150 | 4/1990 |
| JP | 2009-39455 | 2/2009 |
| WO | WO95/16404 | 6/1995 |
| WO | WO96/29044 | 9/1996 |
| WO | WO2004/021958 | 3/2004 |
| WO | WO2004/039205 | 5/2004 |
| WO | WO2005/000477 | 1/2005 |

OTHER PUBLICATIONS

Author Unknown, "NasaFlo Neti Pot," http://www.neilmed.com/usa/nasaflo.php, 1 page, at least as early as Dec. 9, 2009.

Author Unknown, "SinuFlo Ready Rinse," http://www.neilmed.com/usa/sinuflo.php, 1 page, at least as early as Dec. 9, 2009.

Author Unknown, "Sinus Rinse Nasal Wash," http://www.neilmed.com/usa/sinusrinse.php, 3 pages, at least as early as Dec. 9, 2009.

Papsin et al., "Saline Nasal Irrigation," Canadian Family Physician, vol. 49, pp. 168-173, Feb. 2003.

Rabago et al., "Efficacy of Daily Hypertonic Saline Nasal Irrigation Among Patients with Sinusitus: A Randomized Controlled Trial," The Journal of Family Practice, vol. 51, No. 12, pp. 1049-1055, Dec. 2002.

Schumann et al., "Patients Insist on Antibiotics for Sinusitus? Here is a Good Reason to Say 'No'," The Journal of Family Practice, vol. 57, No. 7, pp. 464-468, Jul. 2008.

(56) References Cited

OTHER PUBLICATIONS

The Right Tool, Electron Fusion Devices, Inc., 2 pages, at least as early as Feb. 1991.

Japanese Packaging, 2 pages, at least as early as Dec. 2002.

Japanese Instruction Brochure, 2 pages, at least as early as Dec. 2002.

Brochure: Woog International, "You have a 98% chance of getting gum disease. Unless you read this.", Lancaster, Pennsylvania, Feb. 1987.

Brochure: Woog International, "We put the control of home dental care back into the hands of the professional", Lancaster, Pennsylvania, Feb. 1987.

Brochure: Woog International, "Products at a Glance: Home Dental Care System" Woog Orajet, at least as early as Dec. 18, 1998.

Website: http://www.just4teeth.com/product/Panasonic/Panasonic_Portable_Irrigator.htm, 2 pages, at least as early as Jun. 20, 2003.

Website: http://www.videodirectstore.com/store/merchant.mv?Screen=PROD&Product_Code=EW'. . . , 2 pages, at least as early as Jun. 20, 2003.

Website: http://www.products.consumerguide.com/cp/family/review/index.dfm/id/18742, 2 pages, at least as early as Jun. 20, 2003.

Website: http://www.racekarteng.com/images/walbroparts.gif and http://www.muller.net/mullermachine/docs/walbro1.html, 4 pages, at least as early as Jun. 20, 2003.

International Search Report, PCT/US2010/060880, 2 pages, Feb. 11, 2011.

Waterpik SinuSense, U.S. Appl. No. 29/381,243, Website: http://www.insightsbyapril.com/2012/03/waterpik-natural-remedy-for-sinus.html, retrieved on May 31, 2012.

\* cited by examiner

POWERED IRRIGATOR FOR SINUS CAVITY RINSE WITH DETACHABLE RESERVOIR

CROSS-REFERENCE TO RELATED APPLICATIONS

This continuation application claims under 35 U.S.C. §120 the benefit of U.S. patent application Ser. No. 12/970,345, entitled "Powered Irrigator for Sinus Cavity Rinse" and filed Dec. 16, 2010; as a continuation-in-part of U.S. design application No. 29/352,098, entitled "Powered Irrigator for Sinus Cavity Rinse" and filed Dec. 16, 2009, and as a continuation-in-part of U.S. design application No. 29/364,670 entitled "Faceted Nasal Seal" and filed Jun. 25, 2010, the disclosures of which are hereby incorporated by reference in their entireties. This application claims under 35 U.S.C. §119(e) the benefit of U.S. provisional application No. 61/287,100, entitled "Powered Irrigator for Sinus Cavity Rinse" and filed Dec. 16, 2009, U.S. provisional application No. 61/287,026, entitled "Vessel for Sinus Cavity Rinse" and filed Dec. 16, 2009, and U.S. provisional application No. 61/369,378, entitled "Faceted Nasal Seal" and filed Jul. 30, 2010, the disclosures of which are hereby incorporated by reference in their entireties.

This application is related to U.S. patent application Ser. No. 13/545,838, entitled "Pump for Powered Irrigator for Sinus Cavity Rinse," filed Jul. 10, 2012; U.S. application Ser. No. 12/970,610, entitled "Pot for Sinus Cavity Rinse" filed Dec. 16, 2010, and U.S. patent application Ser. No. 12/970,788, entitled "Bottle for Sinus Cavity Rinse" filed Dec. 16, 2010, and U.S. patent application Ser. No. 12/970,854, entitled "Faceted Nasal Seal" filed Dec. 16, 2010, and U.S. patent application Ser. No. 12/970,415, entitled "Squeeze Bottle for Sinus Cavity Rinse" filed Dec. 16, 2010, and U.S. design application No. 29/381,243, entitled "Powered Irrigator for Sinus Cavity Rinse" filed Dec. 16, 2010, the disclosures of which are herein incorporated by reference in their entireties.

FIELD OF THE INVENTION

This invention relates to powered irrigators for use in rinsing one's sinus cavities.

BACKGROUND

The benefits of rinsing one's sinus cavities have been well established, and include improving resistance to sinus infections, clogged sinuses, allergies, and general health. Oftentimes, however, the articles which one uses to rinse their sinus cavities are difficult to use and make the process unnecessarily difficult and uncomfortable. One of the issues is related to the inability to obtain an effective seal between the nozzle of one of these articles and the user's nasal passage. If the seal is not adequate, during use the fluid can leak from between the nozzle and the nasal passage, thereby making the rinsing process messy.

In addition, the vessels used for sinus rinsing can be difficult to use, and sometimes require challenging coordination. The flow control of the flow from the vessel into the nasal passage has not been adequate in the past, and users have found it difficult to regulate the volume of flow so as to make the rinsing process comfortable. Typical products utilize either gravity flow from a generally large volume of water flowing out of a vessel, or pressurized flow from a squeeze bottle. Both are difficult to accurately control how much liquid is used, and when the liquid flow starts and stops. These products can also require hand strength and dexterity not available to some individuals. And, these products can require bending over a sink or other receptacle at an odd angle, which may be challenging for users with limited flexibility.

It is to satisfy the above-recognized issues that the present invention has been developed.

SUMMARY

The present invention relates to a powered nasal cavity irrigator that includes a main body having a detachably connected handle portion and reservoir portion. The handle portion includes a pump mechanism, power source, and switch for turning on and off the power source to actuate the pump mechanism. Fluid flows from the reservoir portion through the handle portion and out a nozzle disposed at the handle portion upon actuating the pump mechanism. The reservoir includes a generally cylindrical body defining a cavity; and at least two tabs operably connected to the cylindrical body and extending inwards from the cylindrical body towards the cavity. The at least two tabs operably connect the reservoir to the handle portion to releasably secure the reservoir to the handle portion.

The powered nasal cavity irrigator, in one embodiment, includes a rigidly constructed main body having a handle and fluid reservoir detachably connected to each other. An outlet nozzle extends from a top end of the handle. A pump mechanism operably couples to a power source, and a switch is operably couples to the power source for turning the pump mechanism on and off. The switch is arranged at an external surface of the handle, and when the switch turns on the pump mechanism, fluid flows from the fluid reservoir into a first fluid coupling between the reservoir and the pump mechanism and into a second fluid coupling between the pump mechanism to the outlet nozzle.

In another embodiment, a powered nasal cavity irrigator includes a rigidly constructed main body including a handle and fluid reservoir. The handle and the fluid reservoir are detachably connected to each other. A top end of the handle provides a portion being angled relative to a longitudinal axis of the main body. An outlet nozzle extends from the top end of the handle at a substantially right angle to the angled portion of the top end. A pump mechanism operably couples to a power source, and switch operably couples to the power source for turning the pump mechanism on and off. The switch is arranged at an external surface of the handle, and when the switch turns on the pump mechanism, fluid flows from the fluid reservoir into a first fluid coupling between the reservoir and the pump mechanism and into a second fluid coupling between the pump mechanism to the outlet nozzle.

BRIEF DESCRIPTION OF THE DRAWINGS

The features and advantages of the present invention will be more readily apparent from the following detailed description, illustrated by way of example in the drawing figures, wherein.

DETAILED DESCRIPTION

Figure 1:
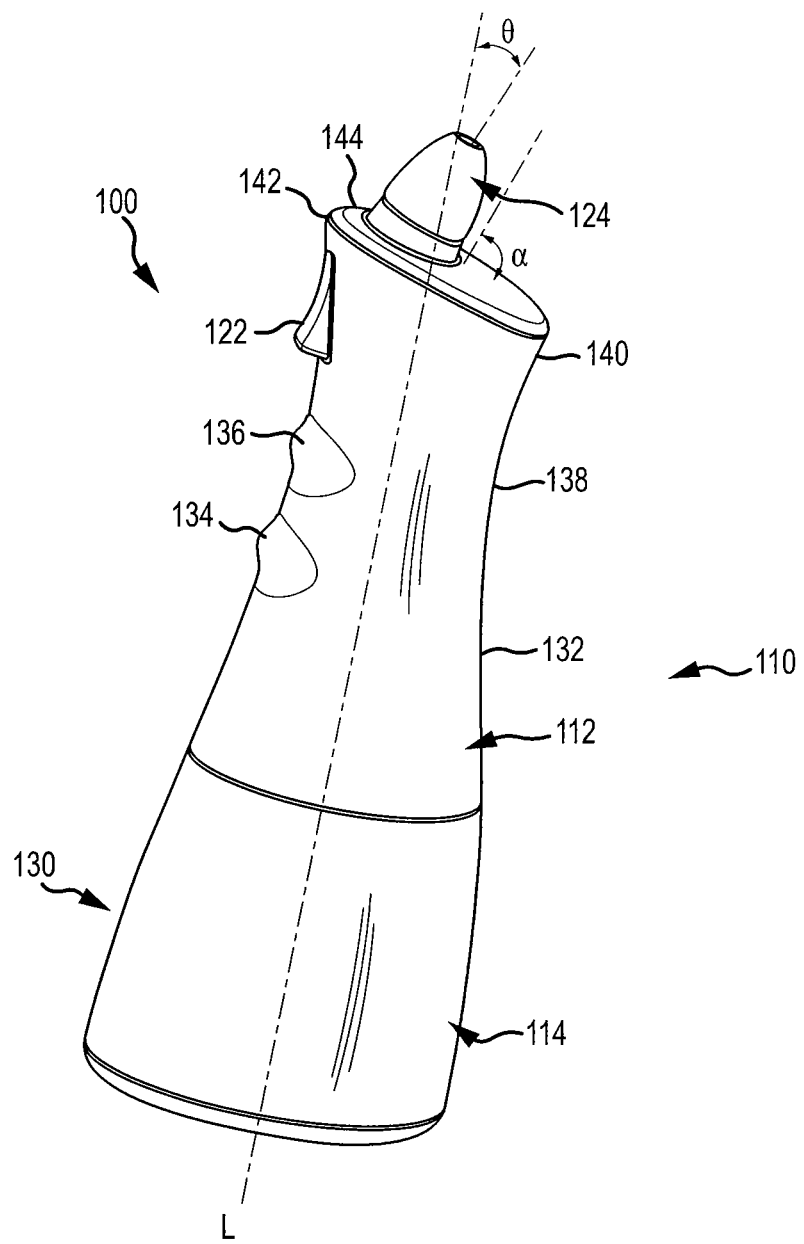
FIG. 1 is an isometric view of the powered irrigator of the present invention.
Figure 2:
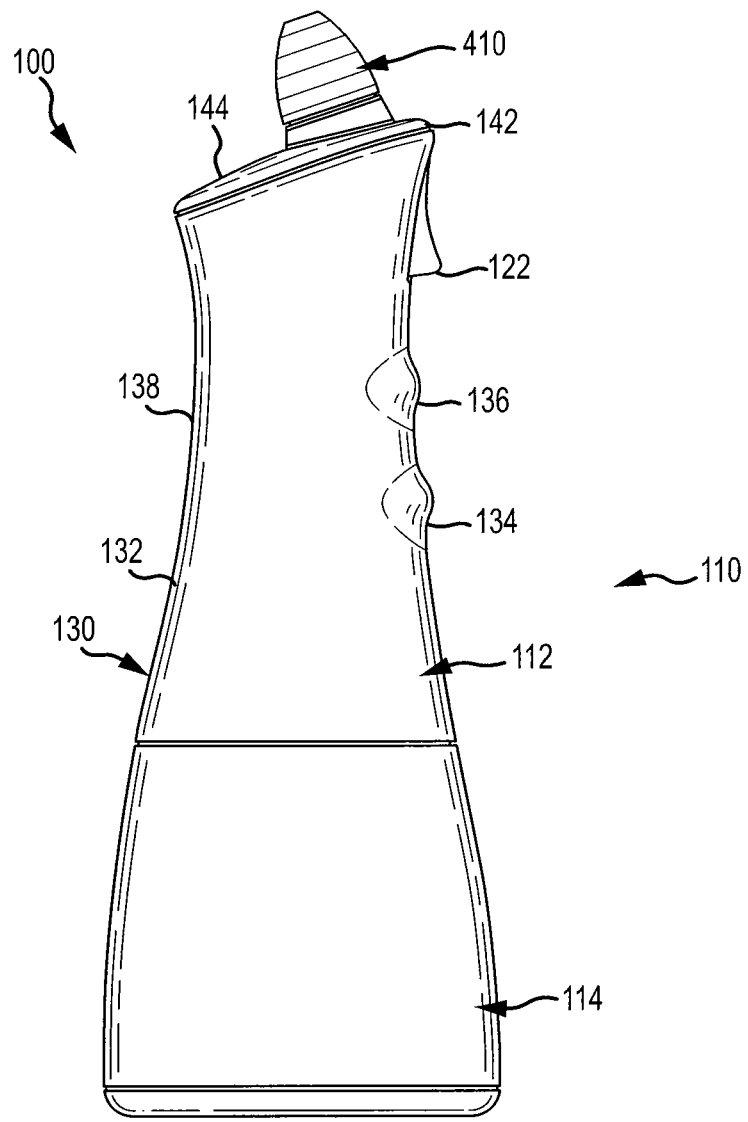
FIG. 2 is an elevation view of the powered irrigator of the present invention with another embodiment of a nozzle.
Figure 3:
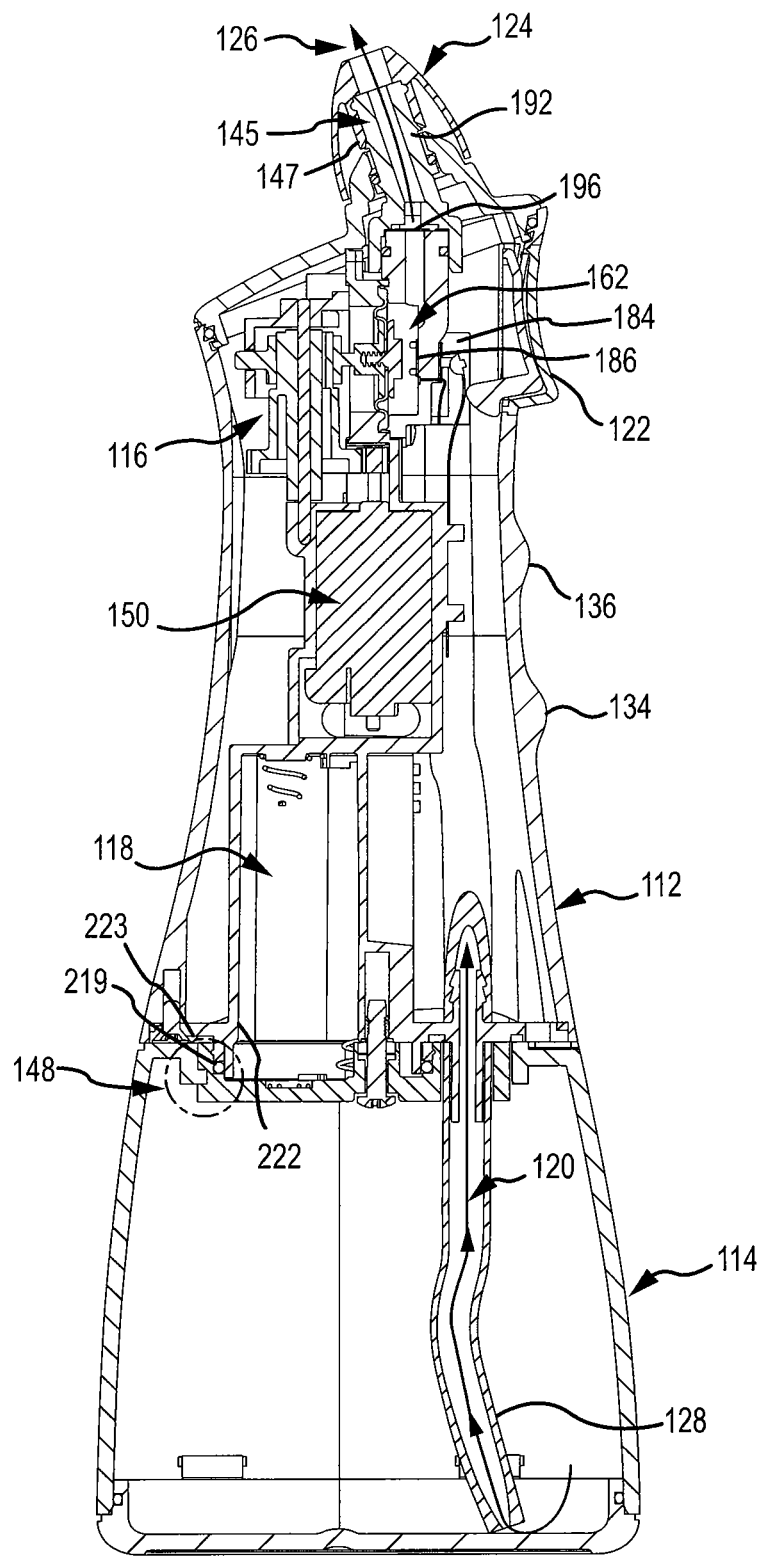
FIG. 3 is a section taken through the irrigator of FIG. 2.

FIGS. 1 and 2 show a powered irrigator 100 for use in rinsing a user's nasal cavities. The irrigator has a main body 110 formed by a top handle portion 112 and a bottom reservoir portion 114. As shown in FIG. 3, the handle portion 112 includes a pump mechanism 116, power source 118 for the pump mechanism 116, fluid flow paths 120 for the fluid to pass up to, through, and from the pump mechanism 116, a switch 122 operably connected to the power source 118 to turn the pump 116 on and off, and a nozzle 124 at the outlet end 126 of the fluid flow paths 120 to comfortably engage and seal with a user's nostril to direct the fluid under pressure into the sinus cavities of the user. The reservoir portion 114 is releasably connected to the top handle portion 112 and holds the rinse solution. A fluid supply tube 128 extends from the pump mechanism 116 into the reservoir portion 114 to draw the rinse solution out of the reservoir portion 114 and into the pump mechanism 116.

The main body 110 has a profiled shape 130 along its length. The width and depth dimension of the reservoir portion 114 is relatively large and rounded about its perimeter. The bottom of the reservoir 114 is relatively flat to allow the main body to sit upright on a support surface. At or just above where the reservoir 114 connects to the handle 112, the dimensions of the main body 110 smoothly decrease to a narrower structure 132 which fits well in the hand. Two contour grip features 134, 136 are positioned below the switch 122 for a user's fingers to engage. The body contours to a minimum dimension 138 approximately in the same position as the top grip feature 136, and then begins to widen out again until the top 140 of the main body, where it flares outwardly.

The switch 122 is positioned just below the rim 142 of the top 140 of the main body. The switch 122 is spring-loaded to thus be actuated upon compression by a user, and automatically terminate actuation upon being released. The top 140 of the main body is planar, and extends or tapers down at an angle facing away from the side where the switch 122 is positioned. The nozzle 124 extends at an angle α, which may be approximately at 90 degrees from the main body 110 top surface 144, and thus at an angle from the longitudinal axis L of the main body 110. This angle between the nozzle extension and the longitudinal axis of the main body allows for a comfortable and convenient orientation of the irrigator 100 relative to a user's nose and face. The angle between the longitudinal axis of the main body 110 and the nozzle 124 extends at an angle θ, which may be about 16 degrees to about 20 degrees, or abut 17.5 degrees.

The nozzle 124 is removable from an end portion 145 formed at the top 140 of the pump mechanism. The nozzle 124 is positioned on the end portion 145 and thus is disposed very near the top surface 144 of the top end 140 of the irrigator 100. This allows for accurate positioning of the nozzle 124 in the user's nostril without the distraction of the nozzle 124 being on the end of a longer jet tip as is known. The nozzle 124 has a collapsible skirt wall 146 (see FIG. 4) for a comfortable fit in the user's nostril. This is described in greater detail below. The low profile positioning of the nozzle 124 on the top 140 of the handle portion 112 provides for a more secure positioning of the nozzle 124. Generally, the nozzle 124 does not extend up from the top surface 144 of the handle 112 more than approximately two height dimensions of the nozzle.

The nozzle 124 has an outer skirt wall 146 having a bottom rim that is free to move, the outer skirt wall 146 will provide a better peripheral fit with the nostril sidewall since the skirt walls 146 are only engaged at the tip 149 and are free to move and flex without being engaged at the free lower end of the outer skirt wall 146. When the nozzle is inserted into the nostril, the outer skirt wall 146 can compress and flex uniquely into the void 205 space between the inner collar 147 of the nozzle 124 (see FIG. 4) and the outer skirt wall 146 of the nozzle 124 and into the void 205 space formed between the skirt wall 146 and the crown 228 formed on the top surface of the irrigator, described below.

FIG. 2 shows the irrigator 100 with a faceted nozzle 410 having a faceted surface that allows the nozzle to create a seal within the nasal cavity better than an oval or purely round nozzle. As described further below in connection with FIGS. 17-19, the faceted or circumferentially stepped nozzle external surface is made up of regions having flat extensions or mixed flat and curved extensions, as the faceted nozzle 410 extends downwards. Like the nozzle 110, the faceted nozzle 410 is self-sealing and is made of a soft elastomeric material, such as food grade silicone rubber.

Figure 4:
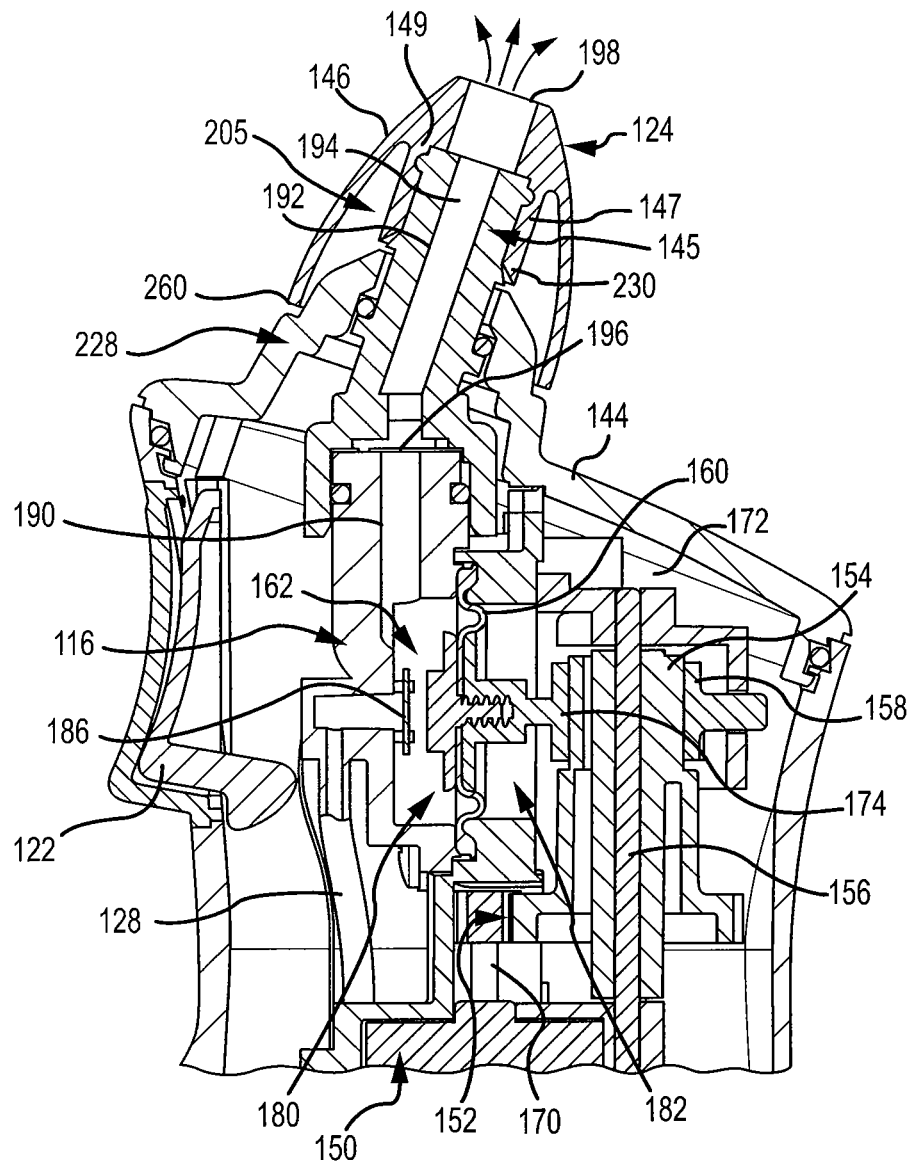
FIG. 4 is an enlarged section similar to FIG. 3.

FIG. 3 is a cross section of the irrigator 100, and shows reservoir portion 114 releasably connected to a bottom rim of the top handle portion 112 by a bayonet latch mechanism 148. The fluid supply tube 128 extends from the reservoir portion 114 into the pump mechanism 116 positioned centrally in the handle portion 112. The pump mechanism 116 is powered by a motor 150, which, as shown in FIG. 4, drives a gear train 152 to actuate an offset cam mechanism 154, which rotates around a cam shaft 156. A cam follower 158 is trained around the cam mechanism 154, and causes the diaphragm 160 to move linearly (i.e., transversely to the longitudinal axis of the irrigator 100) within the compression chamber 162, between an intake stroke and a compression stroke, as is described in more detail below. The main body 110 also includes a power source 118 such as a battery (or batteries). The power source 118 is connected to the motor 150 and the switch 122 to activate the power source 118 upon actuation of the switch 122. The motor 150 has an output shaft 170 that drives a gear train 152, which drives the cam shaft 156 as noted above. A fluid supply tube 128 extends from the handle into the reservoir to allow fluid to be drawn from the reservoir into the pump mechanism 116 upon actuation of the motor 150.

Figure 5:
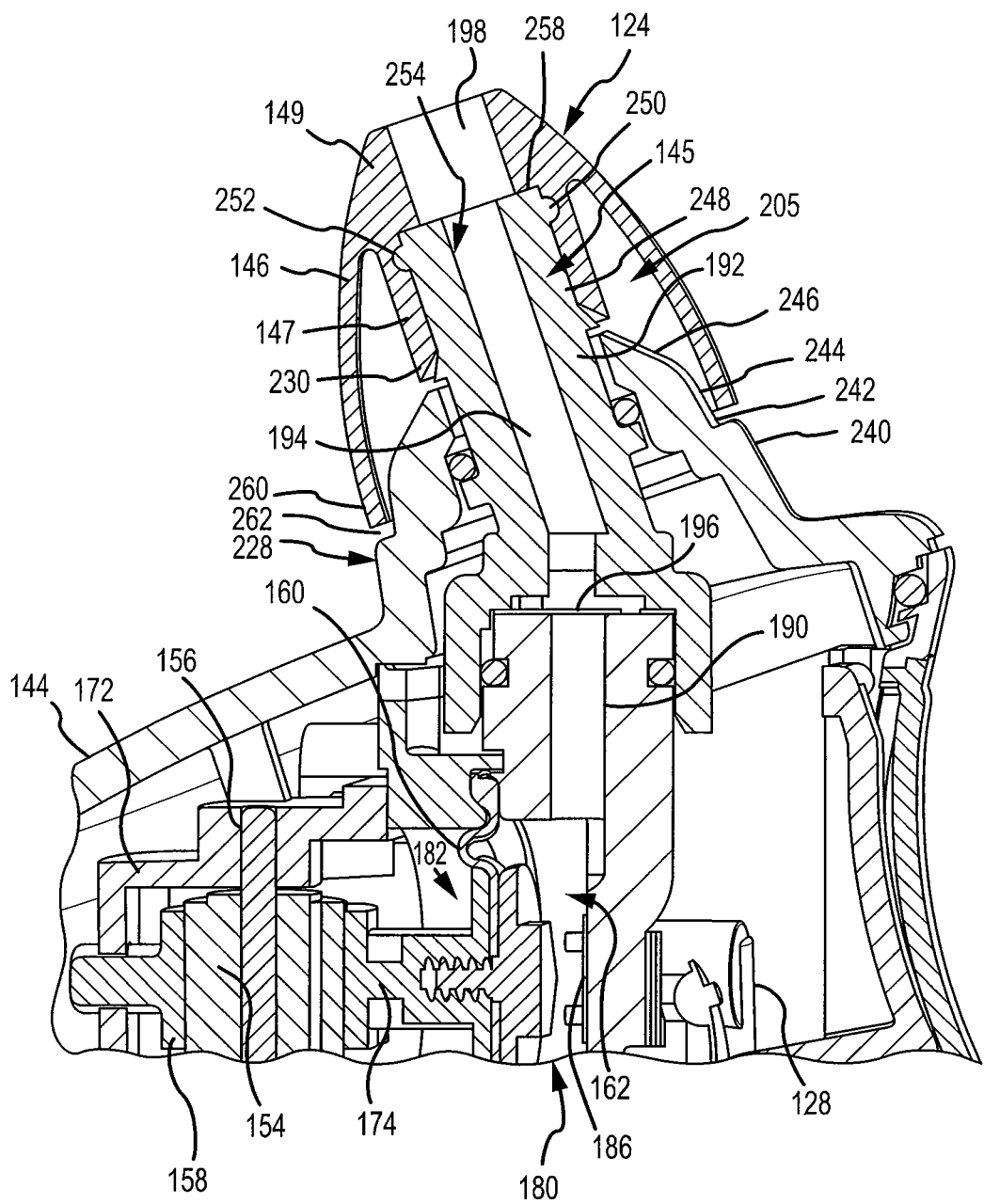
FIG. 5 is a section view similar to FIG. 4.

FIGS. 4 and 5 show the pump mechanism 116 and related structure in more detail. As the motor output shaft 170 turns, the gear train 152 turns such that a gear on the end of the shaft turns a larger gear in a gear reduction relationship. The larger gear of the gear train 152 turns a cam shaft 156, which in turn rotates the offset cam mechanism 154 that rotates with the cam shaft 156. The cam shaft 156 ends are supported in a bearing relationship with a part of the pump mechanism housing 172 located inside the handle 112. The offset cam mechanism 154 is entrained in a cam follower 158. The cam follower 158 includes a pushrod 174 that is connected at one end to the diaphragm 160 positioned in the compression chamber 162 of the pump mechanism 116. The actuation of the cam follower 158 by the offset cam mechanism 154 causes the pushrod 174 to move the diaphragm 160 from an intake stroke (shown in FIG. 6 to a compression stroke (shown in FIGS. 7 and 8) and back, repeatedly. The chamber 180 in the pump mechanism is divided into two regions by the diaphragm 160. The first region 182 behind the diaphragm 160 is primarily to allow the movement of the pushrod 174 and typically does not have fluid in it. The region on the other side of the diaphragm is the compression chamber 162. During the intake stroke, the diaphragm 160 moves toward the first region 182 and enlarges the compression chamber 162. As the compression chamber 162 is enlarged, a vacuum is formed.

The fluid supply tube 128 is in fluid communication with the compression chamber 162 at a fluid inlet 184. An inlet check valve 186 is positioned operably in the connection between fluid supply tube 128 and the compression chamber 162 at the fluid inlet 184 to allow fluid to flow into the compression chamber 162 from the supply tube 128, but not out of the compression chamber 162 into the supply tube 128. Thus, the inlet check valve 186 is open when the diaphragm 160 moves from the compression stroke to the inlet stroke.

Continuing with these same figures, an outlet conduit 190 extends from the compression chamber 162 to a connection portion 192 having a channel 194 formed there through. One end of the connection portion 192 is sealingly engaged with the outlet conduit 190. The other end of the connection portion 192 forms the end portion 145 that receives the nozzle 124 as described above and in more detail below. An outlet check valve 196 is positioned between the end of the outlet conduit and the channel 194 of the connection portion 192. The check valve 196 is open when the pump mechanism 116 moves from the intake stroke through the compression stroke, and is closed when the diaphragm 160 moves from the compression stroke through the intake stroke. The outlet check valve 196 also forms an anti-backflow device to help keep any residual fluid from the nasal passage from flowing back into the pump mechanism 116.

During the intake stroke, a vacuum is formed, which closes the outlet check valve 196 and opens the inlet check valve 186 to allow fluid to be drawn into the compression chamber 162. When the intake stroke is completed, and the compression stroke begins, the positive pressure in the compression chamber 162 causes the inlet check valve 186 to close and the outlet check valve 196 to open, which allows the fluid to be pushed out of the compression chamber 162 and into the outlet conduit 190. From the outlet conduit 190, the fluid flows through the outlet check valve 196 into the channel 194 in the connection portion 192. This channel 194 may have a diameter of 0.110 inches, and is what primarily controls the pressure flow of the outlet flow. From the channel 194 in the connection portion 192 the fluid flows through the nozzle aperture 198 and into the user's nasal cavity. Generally, the pump mechanism 116 runs at about 2000-3000 cycles per minute, with a flow rate of about 500 to 600 ml per minute. The geometry of the flow path 120 creates a relatively low back pressure of approximately 5 psi. This type of pump mechanism 116 is efficient, and allows the generation of the appropriate fluid flows and pressures while drawing relatively little current from the power source 118, such as batteries. Such a pump mechanism 116 may be described as a positive displacement pump that uses a diaphragm. The power source 118 may be permanent, rechargeable or replaceable.

Figure 6:
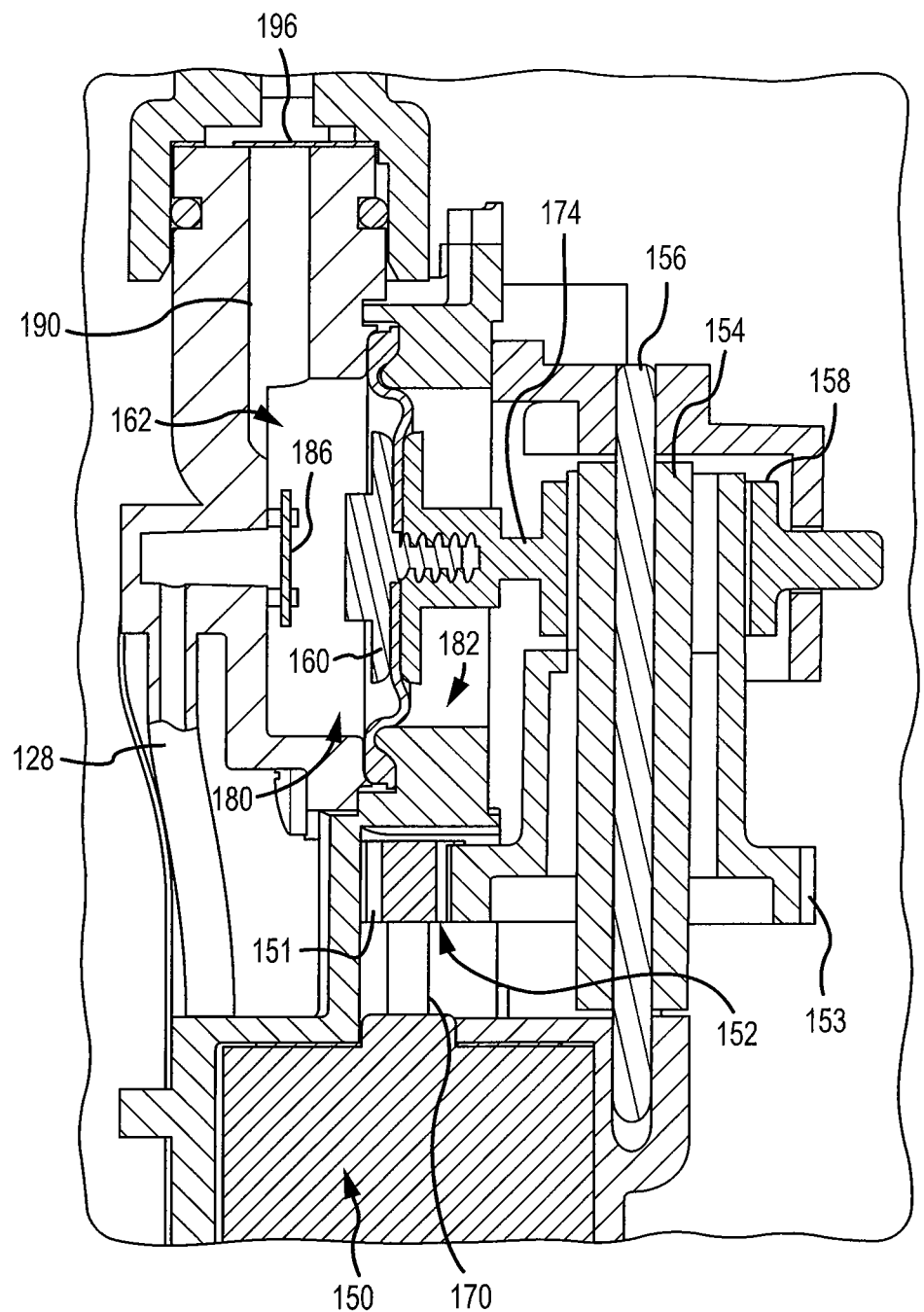
FIG. 6 is a partial section view similar to FIG. 5 with the diaphragm pump at the end of the intake stroke.
Figure 7:
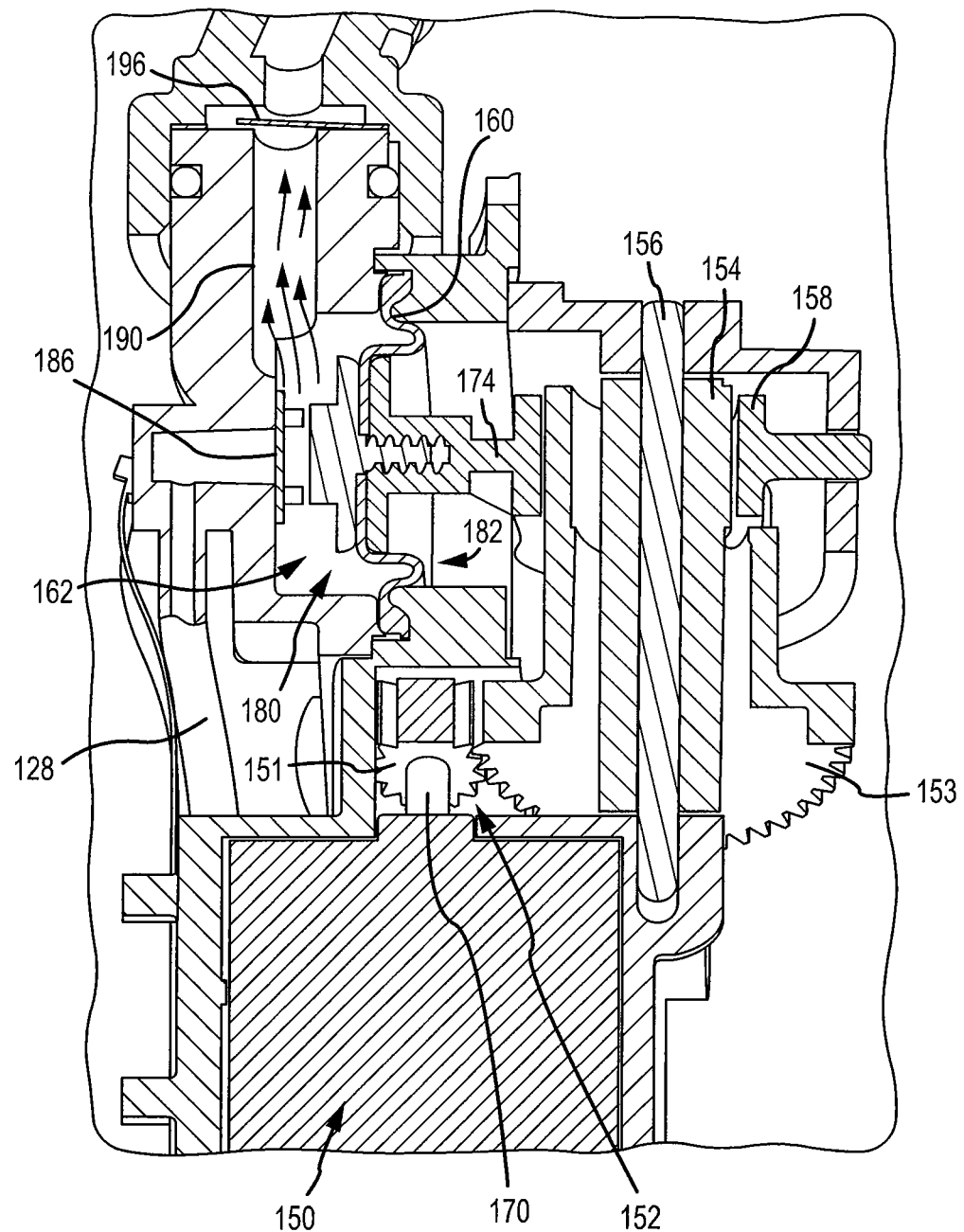
FIG. 7 is a partial section view similar to FIG. 6, with the diaphragm pump at the end of the compression stroke.
Figure 8:
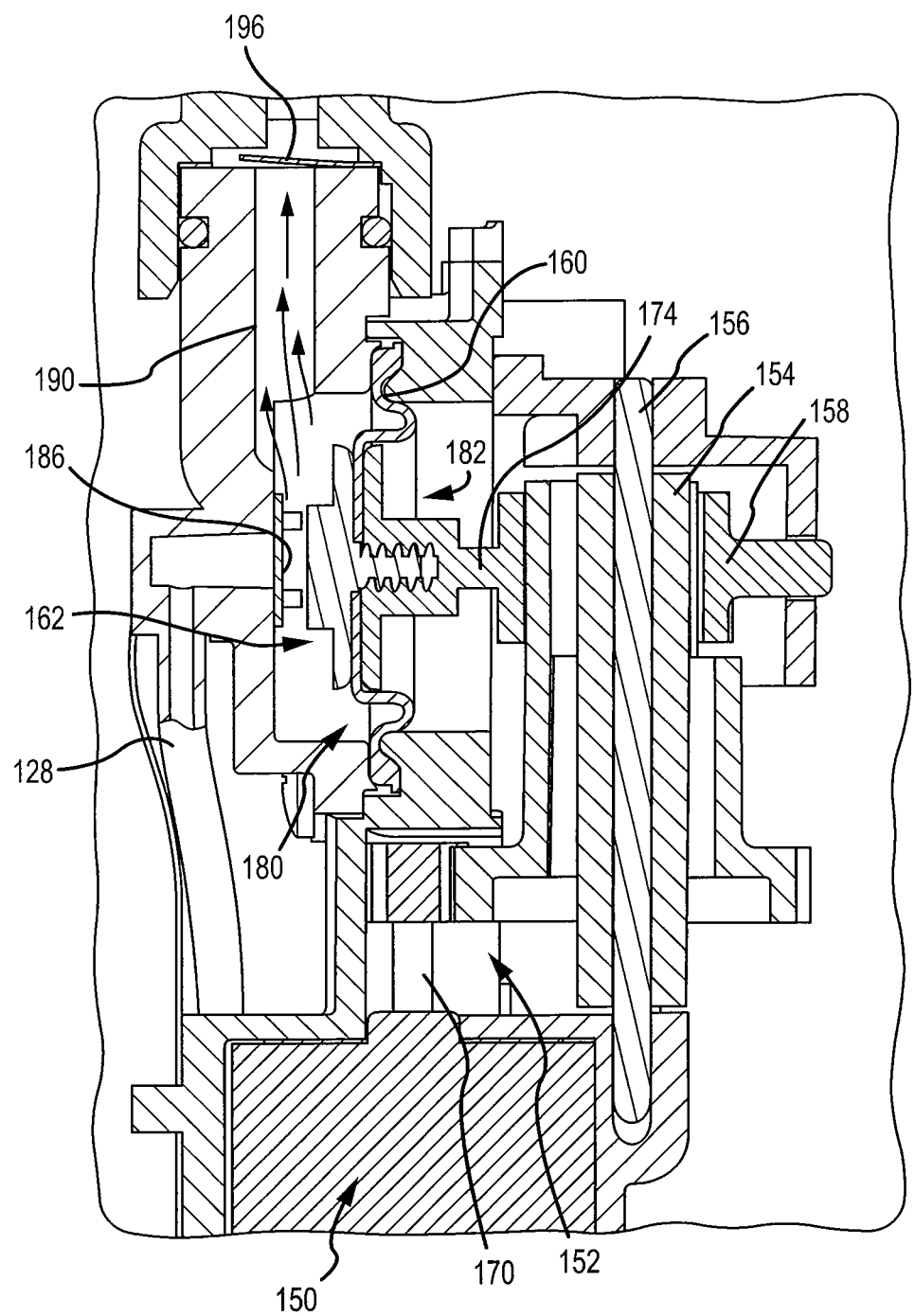
FIG. 8 is a partial section view similar to FIG. 7.

FIG. 6 shows the diaphragm at the end of the intake stroke, where the compression chamber 162 now contains fluid drawn in from the reservoir portion 114 through the supply tube 128 and the open inlet check valve 186. FIGS. 7 and 8 show the diaphragm 160 at the end of the compression stroke, where the fluid has been pushed out of the compression chamber 162 and through the outlet conduit 190 past the outlet check valve 196 into the connection portion 192 and out the aperture 198 of the nozzle 124. In this position, of the diaphragm 160, the inlet check valve 186 is closed, thereby preventing fluid from entering or exiting the inlet check valve 186.

Figure 9:
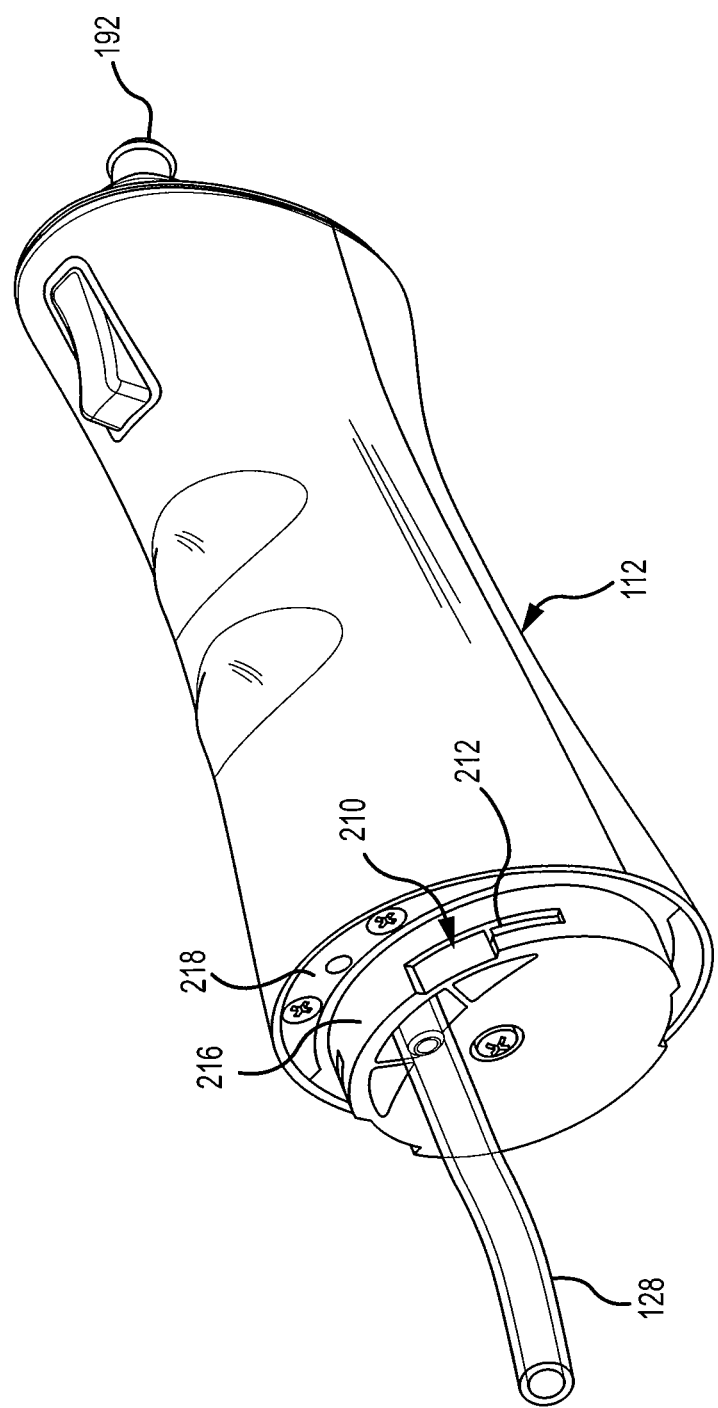
FIG. 9 is an isometric view of the powered irrigator with the reservoir removed.

FIG. 9 shows the handle portion 112 of the irrigator 100 with the reservoir portion 114 removed. The fluid supply tube 128 extends from the end of the handle portion 112 to be positioned in the reservoir portion 114 to draw fluid therefrom. The end of the handle portion 112 includes at least one bayonet latch component 210, in this example a slot 212 for receiving the bayonet tabs 214 formed on the upper rim of the reservoir portion 114 (see FIG. 10). The slot 212 is formed on a rim 216 that extends down from the bottom panel 218 of the handle portion 112. The rim 216 fits within the upper edge 220 of the reservoir portion 114. The power source 118 such as batteries may be replaced in this embodiment by removing the bottom panel 218 of the handle portion 112 to open a cavity 222 (see FIG. 3) for receiving the batteries. With further reference to FIG. 3, at the interface between the bottom panel 218 and the bottom of the handle portion 112 may be provided a sealing element 223 such as an o-ring. For example, the bottom of the handle portion 112 may include a sealing element 223 disposed thereon facing the bottom panel 218 so that when the bottom panel 218 is attached after receiving batteries, a fluid tight seal is provided. The bottom panel 218 may also include a sealing element 219, such as a D-ring disposed within an interior portion of the bottom panel 218, and a protruding wall forming the cavity 222 extending from the bottom of the handle portion 112 may be shaped complementarily to the shape of the sealing element 219 to contact an internal circumference of the sealing element 219. A fluid tight seal may thus be provided between the protruding wall of the handle portion 112 and the bottom panel 218 to prevent fluids from entering the cavity 222.

Figure 10:
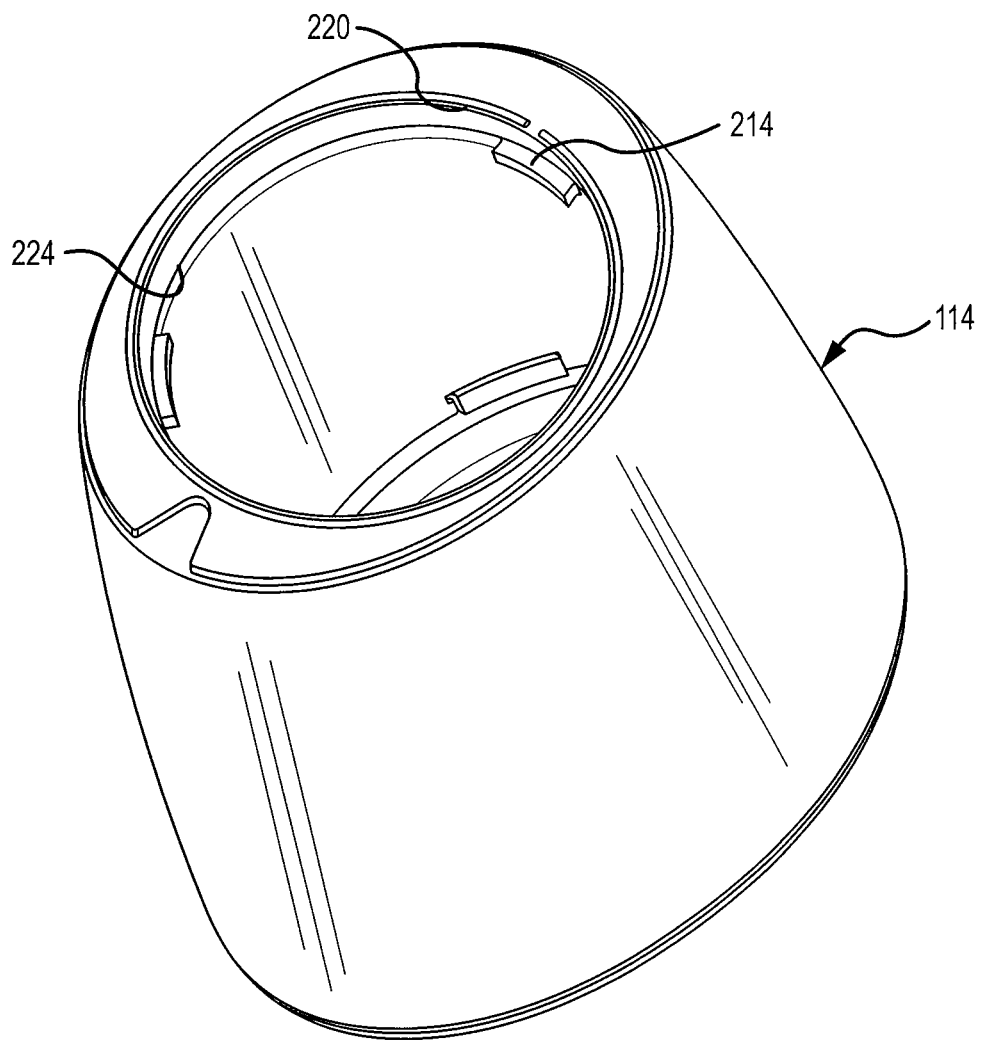
FIG. 10 is an isometric view of the reservoir of the powered irrigator.

FIG. 10 shows the reservoir portion 114 removed from the bottom of the handle portion 112. The upper edge 220 of the reservoir portion 114 forms at least one tab 214 on its inner diameter 224 to be received in at least one slot 212 on the bottom of the handle portion 112 to secure the reservoir portion 114 to the handle portion 112. The tab 214 is secured in the slot by aligning the tab(s) 214 with the slot(s) 212 and rotating the reservoir with respect to the handle to engage the tab 214 in the slot 212. In this way, the entire bottom portion of the main body 110 may be removed to fill the reservoir portion 114 with fluid. The reservoir has a wide opening to make filling the reservoir relatively simple.

Figure 11:
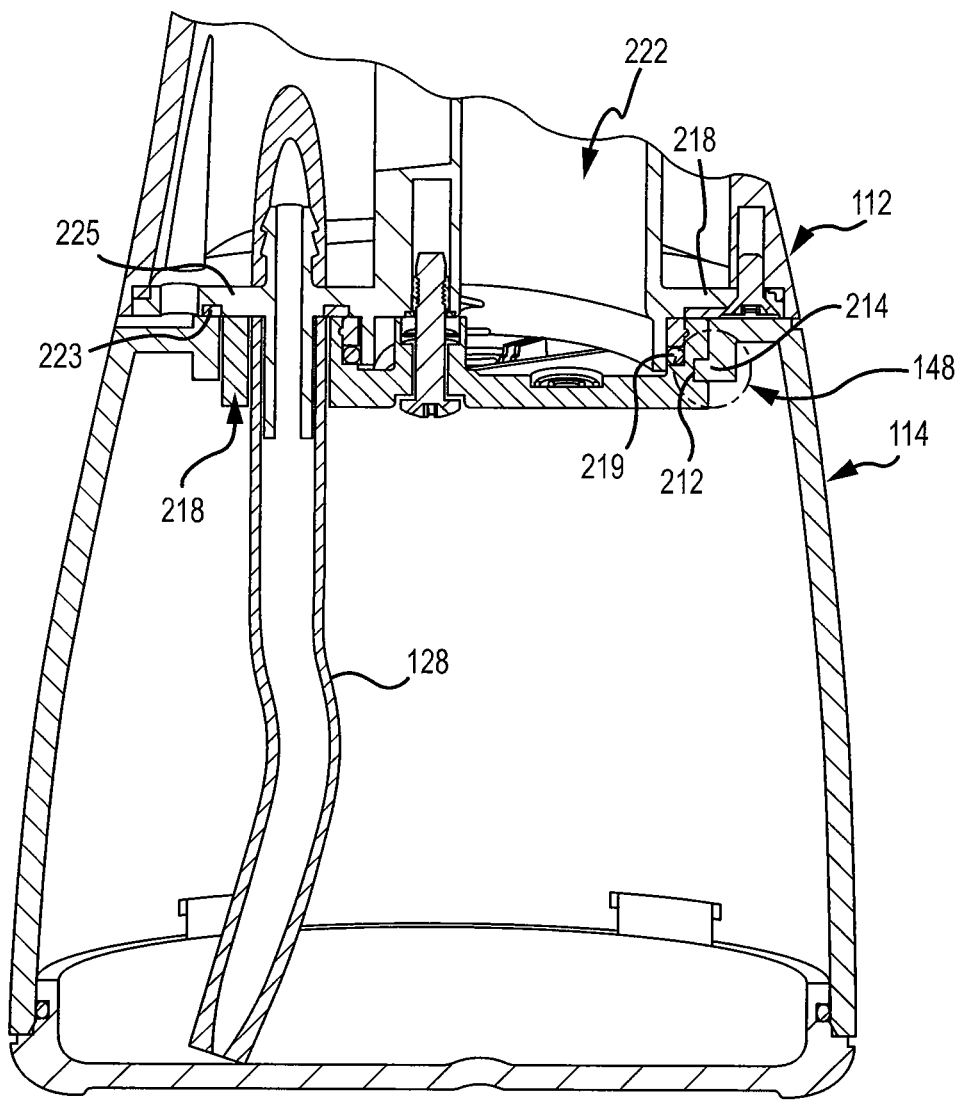
FIG. 11 is a section view of the lower portion of the handle and the reservoir attached by a bayonet connection around the bottom rim of the handle and the top rim of the reservoir.
Figure 12:
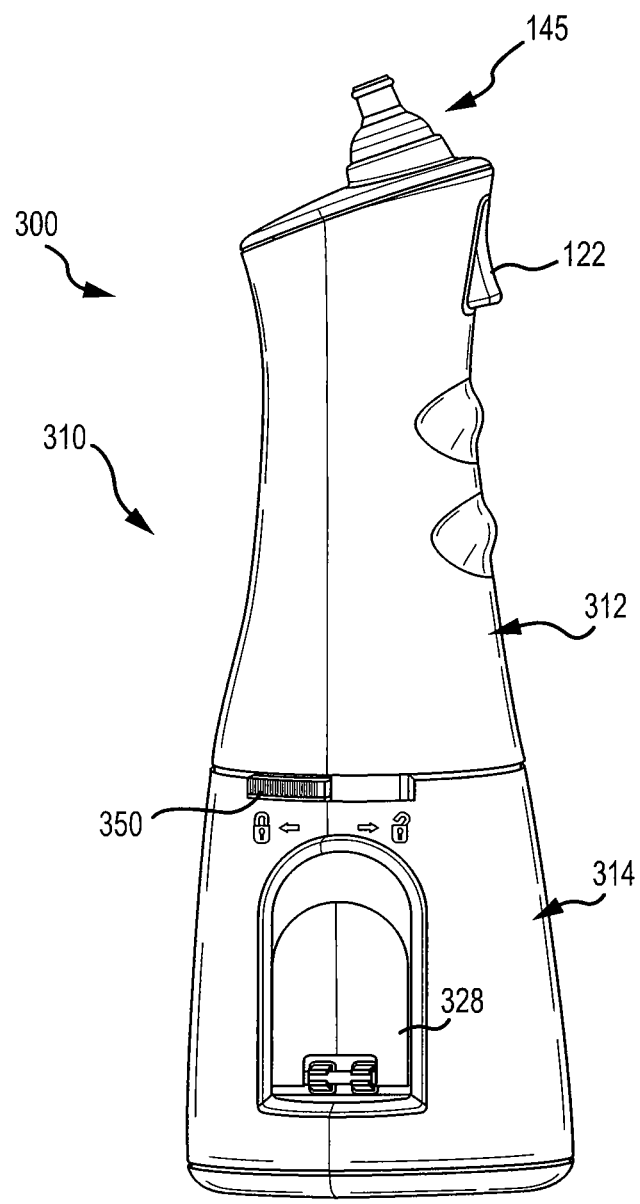
FIG. 12 is an isometric view of another powered irrigator of the present invention.

FIG. 11 shows a cross section of the bayonet latch mechanism 148 in which an assembled engagement is provided between the slot 212 of the handle portion 112 and the tab 214 of the reservoir portion 114. The fluid supply tube 128 may be continuous, or may extend through the bottom panel 218 of the handle portion 112 by a tubular fitting 225.

Returning to FIG. 5, the end portion 145 is formed at an exterior surface of the irrigator 100, receives the nozzle 124. The end portion 145 includes both the distal end of the connection portion 192 and the crown 228. The connection portion 192 forming a part of the end portion 145 is an exposed distal end that extends through the crown 228. The proximal end of the connection portion 192 is recessed within and sealingly engages with the handle portion 112, and at a terminal end, the connection portion 192 engages with the distal end of the outlet conduit 190, described above.

The end portion 145 extends or protrudes upwardly from the angled top surface 144 of the irrigator and receives the nozzle 124. The end portion 145 at the proximal end of the crown 228 includes a base section 240 having a first diameter, a shoulder 242 formed annularly around the base section 240 extending to a decreased diameter to form a first portion 244 of the end portion 145, which then transitions into the conical section 246 extending further away from the base section 240 and tapering down and decreasing the diameter even further until the second portion 248 formed by the connection portion 192, where the second portion 248 forms a cylindrical wall and extends away from the conical section 246. An annular rib 250 is formed on the outer diameter of the second portion 248. The base section 240, first portion 244 and the second portion 248 are generally cylindrical in shape, with the inner diameters and outer diameters being largest at the base portion 240, somewhat smaller for the second portion 244, decreasing with the angle of the conical section 246, down to the size of the second portion 248. The conical section 246 is formed by both the tapering portion of the crown 228 as well as a tapering proximal section of the exposed connection portion 192.

The outer diameter of the second portion 248 forming the annular rib 250 is about the same diameter as the inner diameter of the inner collar 147 of the nozzle such that when the nozzle 124 is positioned over the second portion 248, the inner collar 147 of the nozzle engages the outer walls of the second portion 248, and the rib 250 of the second portion 248 snaps into the annular channel 252 formed in the inner diameter of the inner collar 147 to hold the nozzle 124 onto the end portion 145 at a predefined position. This engagement structure 254 allows secure placement of the nozzle 124 on top of the end portion 145, but allows it to be removed for cleaning or replacement if desired.

When the nozzle 124 is positioned on the end portion 145, the aperture 198 of the engagement tip 149 aligns with the aperture 210 formed in the second portion 248 of the end portion 145. The terminal edge 230 of the inner collar 147 of the nozzle may engage the outer wall of the conical section 246 somewhat near the intersection between the conical section 246 and the second portion 248 of the end portion 145. The terminal edge 230 of the inner collar 147 may be beveled at an angle complementary to the angle of the conical section 246 of the end portion 145 to connect with the conical section 196 and to provide sealing. The engagement of the terminal edge 230 of the inner collar 147 provides additional sealing to help keep the fluid flowing through the end portion 145 and the nozzle 124 and from passing between the engagement of the nozzle 124 and the second portion 248. In the predefined position of the nozzle, the end of the second portion 248 also engages a shoulder 258 formed in the tip 149 of the nozzle, with the shoulder 258 being formed around the aperture 198 extending through the tip 149. The tip 149 of the nozzle is solid in the area surrounding the aperture 198 extending through the tip 149. However, the outer wall extending downwardly and away from the tip 149 forms an outer skirt 146, starting at about the position from where the inner collar 147 extends downwardly from the base of the tip 149. An annular spacing or void 205 is formed between the outer skirt 146 and the inner collar 147 and between the outer skirt 146 and the conical section 246. That is, the void space 205 is formed in the area of the nozzle 124 between where the outer skirt 146 and inner collar 147 extend down, and because the wall forming the outer skirt 146 extends further from the tip 149 than does the wall forming the inner collar 147, the continuing void 205 is formed between the skirt 146 and conical section 246 beyond the terminal edge 230 of the inner collar 147. The terminal edge 260 of the skirt 146 is positioned around the first portion 244 of the end portion 145. The terminal edge 260 of the skirt, as well as the adjacent wall structure of the skirt 146, closely fits with the first portion 244 of the end portion but does not necessarily engage the first portion 244. Also, a gap 262 may be formed between the shoulder 242 extending between the base portion 240 and the first portion 244 and the terminal edge 260 of the skirt. The terminal edge 206 of the skirt 146 does not attach to or otherwise affix to the first portion 194 of the end portion 145 and may move relative thereto. The inner collar 147 connects to the end portion 145 at a position closer to the tip 149 of the nozzle and is spaced above the edge of the skirt wall.

The nozzle 124 is made of a soft elastomeric material, such as food grade silicone rubber. The skirt 146, when positioned in the user's nasal passage, flexes inwardly into the void space 205 formed between the skirt 146 and the inner collar 147 and the void space 205 between the skirt 146 and the conical section 246 and may do so radially and/or irregularly around its circumference in order to closely match the shape of the user's nostril. This helps create an adequate seal between the user's nostril and the self-sealing nozzle structure. When the nozzle 124 is removed from the user's nostril, the elastomeric material springs back into its original shape. The wall thickness of the skirt 146 is 0.040 inches and the wall thickness of the inner collar 147 is 0.060 inches. The gently curving, cone-like shape of the nozzle 124 from the tip 149 down to the terminal edge 260 of the skirt allows for a close fit with a variety of sizes of nasal passages. The void space 205 may be annular, or may be discontinuous within the skirt wall.

One feature that allows the skirt structure to provide an adequate seal for the user's nasal passages is the engagement of the terminal edge 260 of the skirt with the first portion 244 of the end portion 145. When the nozzle 124 is inserted into the user's nasal passage, and the skirt 146 compresses radially inwardly to conform to the shape of the user's nasal passage, the terminal end 260 of the skirt engages the first portion 244 of the end portion 145 and keeps that portion of the skirt 146 from deflecting further inwardly, thus providing some structural rigidity to the flexion of the portion of the skirt 146 extending between the tip and the terminal end. This provides some resistance to flexure to help create a firm but comfortable fit of the nozzle 124 within the user's nasal passage, and also facilitates the rebound of the skirt 146 back to its original shape after being removed from the user's nasal passage. However, the terminal end 260 is not joined to first portion 244 and may move relative thereto.

FIGS. 12-16 show another embodiment of an irrigator 300 with a main body 310 including a handle portion 312 connected to a reservoir portion 314. The reservoir portion 314 differs from the reservoir portion 114 described above in connection with FIGS. 1-11 by the reservoir portion 314 addition of a locking ring 320 movably held in the reservoir portion by the retaining ring 322, a tab 324 formed on the locking ring 320, a reservoir outlet 326, and a reservoir flip cap 328 covering a reservoir sidewall aperture 330 forming a reservoir inlet. The handle portion 312 differs from the handle portion 112 described above in connection with FIGS. 1-11 by the handle portion 312 modification of the handle portion fluid flow path 332, which includes a recessed tubular fitting 334 configured to receive the reservoir outlet 326 of the reservoir portion 316. The handle portion 312 is similar to the handle portion 112 in other respects, and includes a pump mechanism 116, power source 118 for the pump mechanism 116, a switch 122 operably connected to the power source 118 to turn the pump 116 on and off, and receives a nozzle 124 (not shown) at the end portion 145.

Figure 13:
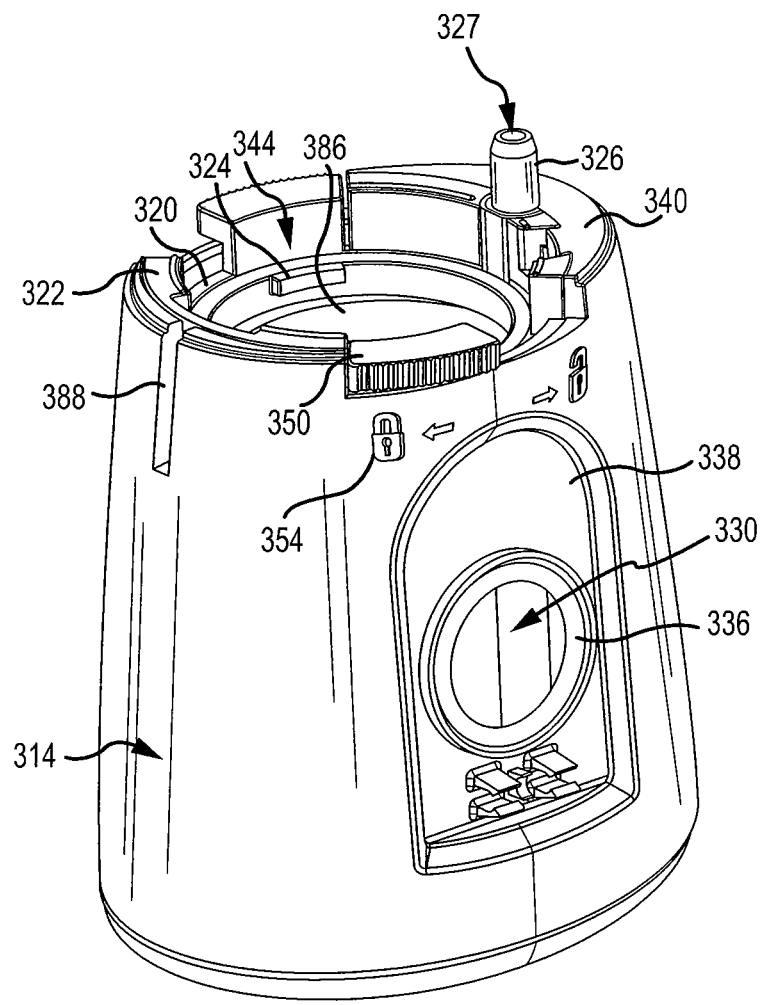
FIG. 13 is an isometric view of the reservoir of the powered irrigator of FIG. 12.
Figure 14:
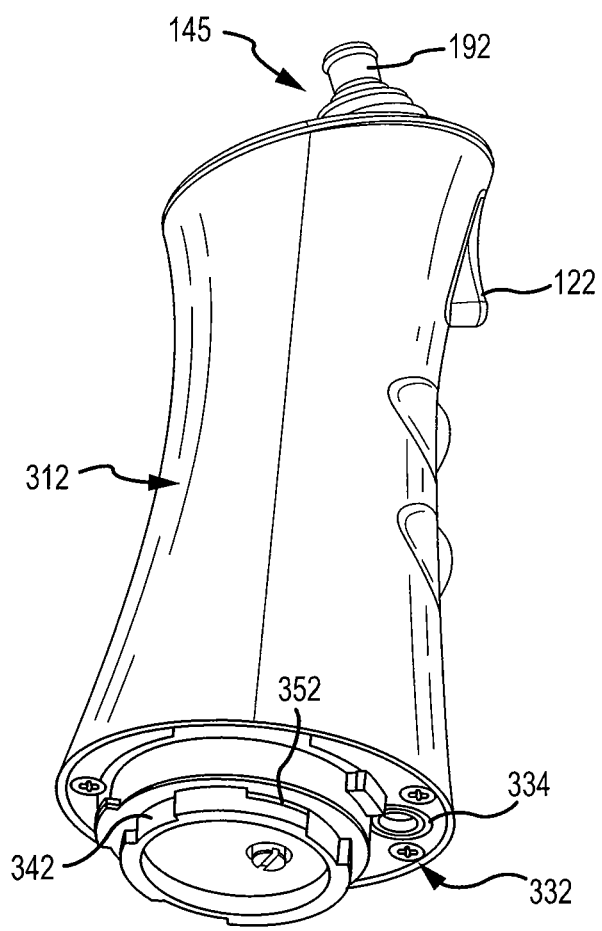
FIG. 14 is an isometric view of the handle of the powered irrigator if FIG. 12.
Figure 15:
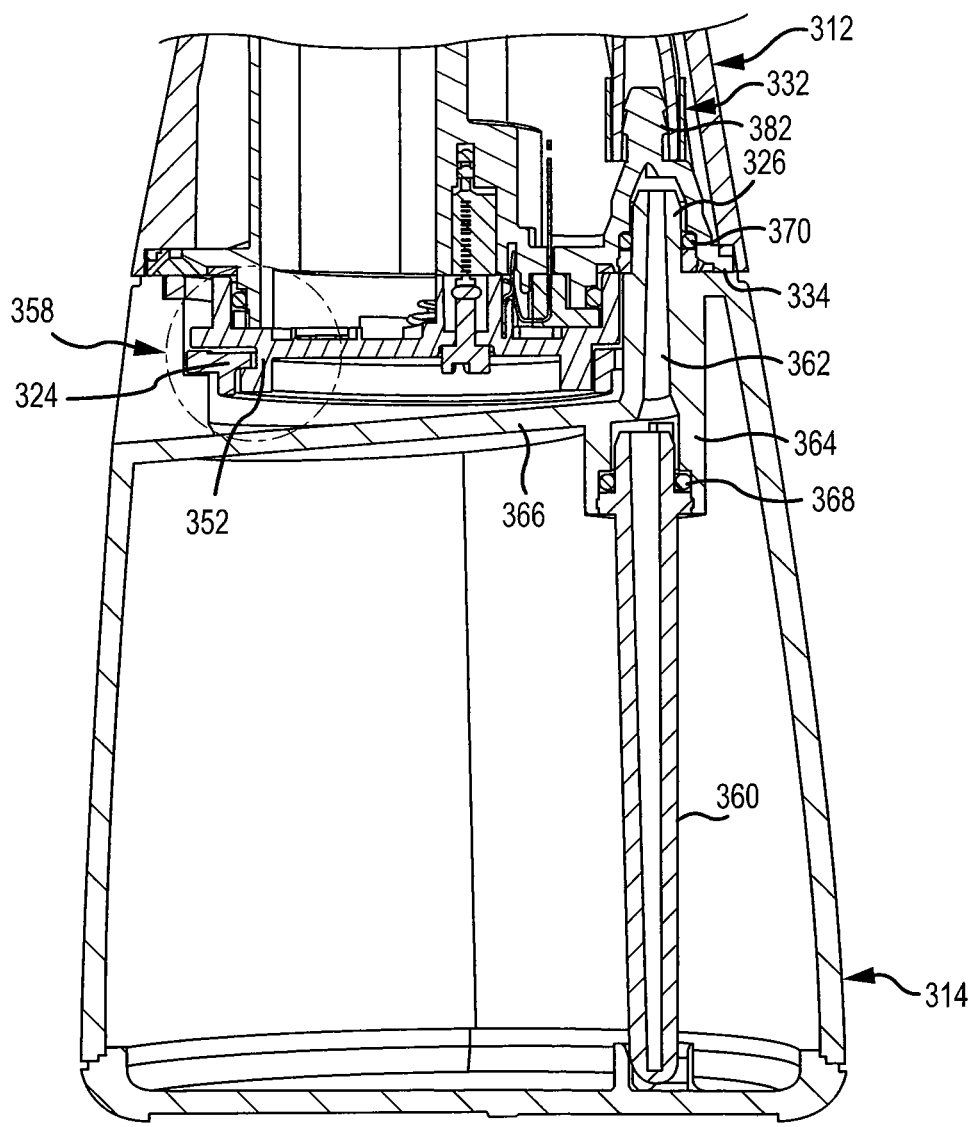
FIG. 15 is a partial section taken through the irrigator of FIG. 12.

With reference to FIGS. 13 and 15, the reservoir part 314 is configured as a substantially enclosed structure forming an inlet and a relatively small outlet. The sidewall aperture 330 defines the reservoir inlet for the reservoir part 314. The sidewall aperture 330 includes a sealing ring 336 such as a silicone grommet extending between an interior and an external recessed portion 338 of the reservoir part 314. The sidewall aperture 330 allows the reservoir part be opened when the flip cap 328 is rotated down or flipped away from the reservoir part 314, and the sidewall aperture 330 is fluidly sealed by the reservoir flip cap 328 (see FIG. 12) mating with the sealing ring 336 when the reservoir flip cap 328 is pressed into the recessed portion 338. When the reservoir is to be filled with the rinse solution, the user rotates the flip cap 328 away from the recessed portion 338 and pours the rinse solution through the sidewall aperture 330 and into the substantially enclosed interior of the reservoir part 314. As described further below, the cylindrical tubular-shaped reservoir outlet 326 projects vertically from a top surface 340 of the reservoir part 314 and provides fluid access to the handle portion 312.

When the reservoir portion 314 is to be connected to the handle portion 312, the reservoir outlet 326 is aligned with the recessed tubular fitting 334 and the handle portion 312 first connects to the reservoir portion 314 by forming a connection by the recessed tubular fitting 334 receiving the reservoir outlet 326. As this connection is formed, the rim 342 forming the bottom of the handle portion 312 is inserted into an upper circumferential recess 344 formed in the reservoir portion 314. The locking ring 320 is rotatable from an unlocked position to a locked position, and during the fitting process, the locking ring 320 is rotated by a user moving the sliding flange 350 to the unlocked position in which the tab 324 of the locking ring 320 is arranged so that the rim 342 passes into the circumferential recess 344. Upon fitting the reservoir outlet 326 to the recessed tubular fitting 334 and arranging the rim 342 in the circumferential recess 344, the user slides the locking ring flange 350 to the locked position in which the tab 324 of the locking ring enters the slot 352 formed in the rim 342 of the handle portion. The user is able to identify whether the flange 350 is in a locked or an unlocked position by aligning the flange 350 with the lock and unlock indicia 354 arranged on the external surface of the reservoir portion 314. The locking ring 320 is held on the reservoir portion 314 by the retaining ring 322.

FIG. 15 shows a cross-section of the handle portion 312 connected to the reservoir portion 314 in a locked position of the bayonet latch mechanism 358 established between the slot 352 and the rim 342. In the locked position of the locking ring 320, the tab 324 of the locking ring 320 has been rotated to enter the slot 352 in the handle portion 312 and locks the handle portion 312 to the reservoir portion 314. Thus, if a user attempts to rotate the handle portion 312 or the reservoir portion 314 relative to the other, the bayonet latch mechanism 358 engaged in the locked position prevents the portions from relative rotation and from detaching. If the user desires to detach the handle portion 312 from the reservoir portion 314, the flange 350 is simply shifted in the direction transverse to the longitudinal axis of the main body 310.

Figure 16:
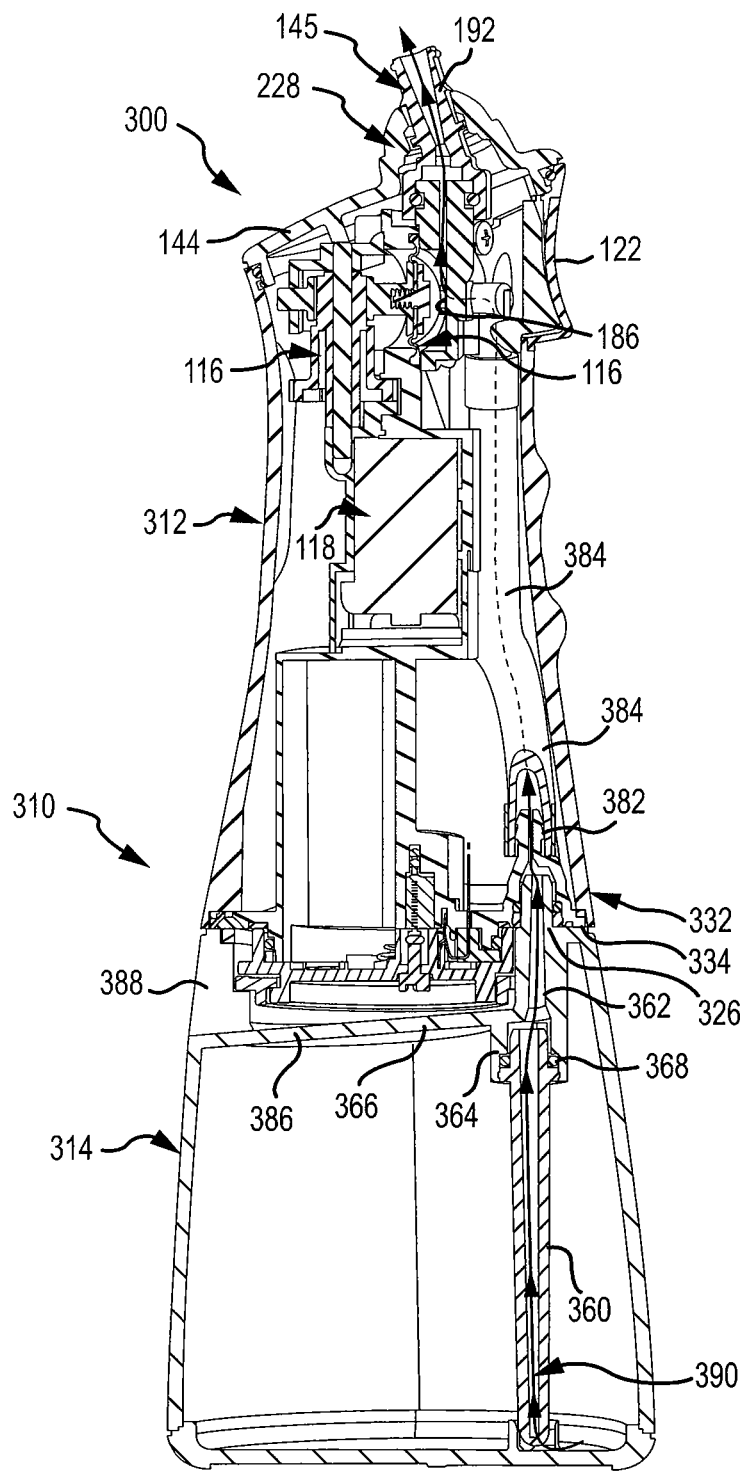
FIG. 16 is a section view of taken through the irrigator of FIG. 12.

In FIG. 16, a fluid intake tube 360 connects to a passage 362 of the reservoir outlet 326 at a tubular fitting 364 projecting from a top enclosing wall 366 of the reservoir portion 314. The projecting tubular fitting 364 receives the fluid intake tube 360 within its internal circumference. An annular seal 368 is provided around an external circumference of the fluid intake tube 360 and the internal circumference of the tubular fitting 364 in order to facilitate providing a fluid tight connection between the fluid intake tube 360 and the reservoir outlet 326. The reservoir outlet 326 and the recessed tubular fitting 334 of the handle portion 312 establish a fluid tight connection, which is facilitated by the annular seal 370 disposed in an internal circumference of the tubular fitting 334 that seals around the external circumference of the reservoir outlet 326 upon insertion of the reservoir outlet 326 into the tubular fitting 334. The fluid connection 332 of the handle portion 312 includes a projecting tubular fitting 382 that is configured to fit within a fluid passage 384 leading from a bottom of the handle portion 312 to the pump mechanism 116. Accordingly, when a user presses the switch 122, the power source 118 actuates the pump mechanism 116, which draws the rinse solution from the reservoir portion 314. The rinse solution follows a fluid pathway 390 from the fluid intake tube 360 into passage 362 and exits the reservoir portion 314 at the reservoir outlet 326, which empties into the recessed tubular fitting 334 of the handle portion 312 and continues into the projecting tubular fitting 382 and through the fluid passage 384. When the inlet check valve 186 is in an opened position, the solution enters the pump mechanism 116 for delivery from the nozzle 124.

The reservoir portion 314 includes a sloped floor 386 recessed from the top surface 340. The sloped floor 386 terminates the upper circumferential recess 344, and encloses the interior of the reservoir portion 314. The sloped floor 386 extends downwardly at an angle as it extends away from the area of the reservoir portion 314 carrying the reservoir outlet 326. At the bottom end of the downward sloped floor 386, the reservoir part forms a slit 388 leading to the exterior of the reservoir portion 314 that extends vertically to the top surface 340. The slit 388 in combination with the downward sloping floor 386 allows fluid escaping the reservoir portion 314, for example via the reservoir outlet 326, to be carried by gravity down the sloped floor 386 and out the slit 388. This allows fluid to escape from the reservoir portion 314 before the fluid can enter the cavity 222 holding the power source 118.

Because the reservoir portion 314 is a substantially enclosed structure, the fluid pathway 390 of irrigator 300 differs from the fluid pathway 120 of irrigator 100. In irrigator 100, the fluid supply tube 128 extends from handle portion 112 into the opening defined by the upper edge 220 of the reservoir portion 114. Thus, the fluid pathway 120 of irrigator 100 is substantially provided by components associated with the handle portion 112. In contrast, the fluid pathway 390 of irrigator 300 includes components within both the handle portion 312 and the reservoir portion 314. The irrigator 300, like the irrigator 100 includes a pump mechanism 116, power source 118 for the pump mechanism 116, switch 122 operably connected to the power source 118 to turn the pump 116, but in irrigator 300, these components cooperate to draw fluid through fluid pathway 390 described above for delivering the rinse solution from the nozzle.

Figure 17:
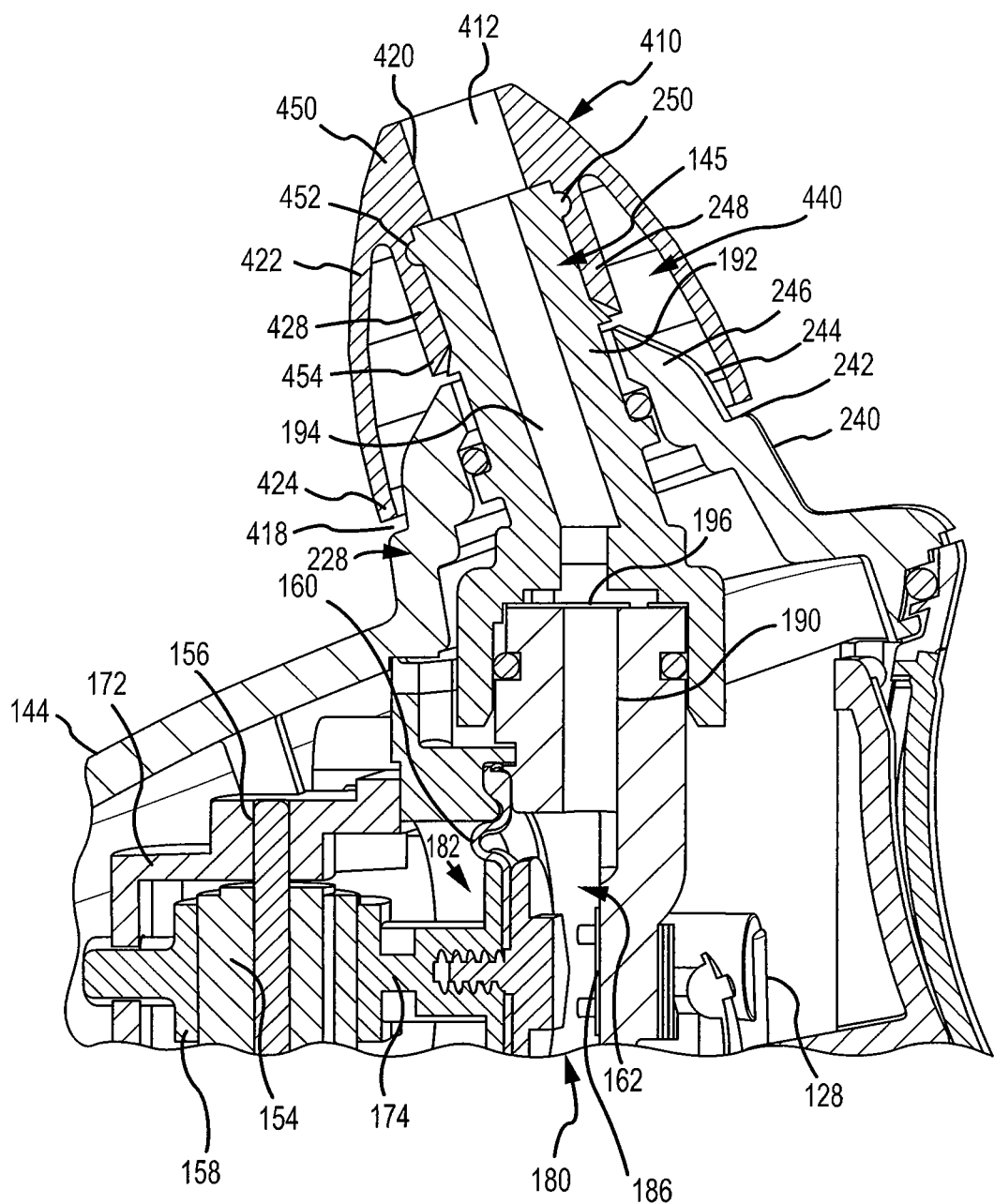
FIG. 17 is a section view of the irrigator of FIG. 1 with the nozzle of FIG. 2.

FIG. 17 is a section view of the faceted nozzle 410 of FIG. 2 attached to the irrigator 100 by the end portion 145. The faceted nozzle 410 has a skirt 422 that extends outwardly and away from a tip 450, an inner collar 428 extending downwardly and away from the tip and forms a cylindrical wall 420 creating a conduit or passageway within the inner surface of the faceted nozzle 410. The inner collar 428 may be formed integrally with the skirt 422. The inner collar 428 may terminate at the tip 450 creating the outlet aperture 412. The distal end of the inner collar 428 terminates inside the skirt 422. In some implementations the inner collar 428 may extend as far as the terminal edge 424 of the skirt 422 and in other implementations (such as the implementation illustrated in FIG. 17) the inner collar 428 may have a terminal edge 454 that terminates at a point above the terminal edge 424 of the skirt 422. The wall thickness of the inner collar 428 in some embodiments may be approximately 0.060 inches.

As can be seen from FIG. 17, the inner collar 428 of the faceted nozzle 410 connects with the end portion 145 formed by the crown 228 and the connection portion 192. The faceted nozzle 410 is placed above the end portion 145 and the end portion 145 may be inserted partially into the inner collar 428. In some implementations the end portion 145 may extend only partially into the inner collar 428. Furthermore, an o-ring (not shown) may be secured within the annular recess 452 to create a fluid-tight seal between the inner collar 428 and the end portion 145.

The skirt 422 extends away from the second portion 248 and the inner collar 428 creating a void 440 or open space between the conical section 246 of the end portion 145 and the skirt 422. The void 440 or annular spacing is also formed between the skirt 422 and the inner collar 428, and the wall forming the skirt 422 extends further from the tip 450 than does the wall forming the inner collar 428 such that the terminal edge 424 of the skirt 422 is positioned around a cylindrical first portion 244 of the end portion 145. The void space 440 may be annular and may be continuous or discontinuous within the skirt wall.

The terminal edge 424 of the skirt 422, as well as the adjacent wall structure of the skirt 422, may closely fit with the cylindrical first portion 244 of the end portion 145, but not necessarily engage with the cylindrical first portion 244. Also, a small gap 418 may be formed between the shoulder 242 of the end portion 145 and the terminal edge 424 of the skirt 422. As discussed above, the terminal edge 424 of the skirt 422 may not attach to or otherwise be affixed to the cylindrical first portion 244 and may move relative thereto. In other implementations the skirt 422 may rest along the cylindrical first portion 244 or otherwise contact the cylindrical first portion 244 of the end portion.

The inner collar 428 extends downward from the outlet aperture 412 and may mate and fluidly connect with the end portion 145, attaching the faceted nozzle 410 to the irrigator 100. The inner collar 428 may include an annular recess 452 along its inner walls to receive the circumferential rib 250 on the second portion 248 of the end portion 145. The terminal edge 454 of the inner collar 428 may be beveled at an angle complementary to the angle of the conical section 246 of the end portion 145 to connect with the conical section 196 and to provide sealing. The terminal edge 454 of the inner collar 428 may connect with the conical section 246 to provide additional sealing and help keep the fluid flowing through the end portion 145 and the faceted nozzle 410 and prevent fluid from passing between the engagement of the faceted nozzle 410 and the second portion 148.

The tip 450 of the faceted nozzle 410 above the annular recess 452 extends down to a cylindrical wall 420 that defines the outlet aperture 412 and the tip 450 may be thicker than the wall of the inner collar 428, the inner collar 428 thus may have a larger inner diameter than the cylindrical wall 420 forming the outlet aperture 412. A shoulder 426 formed in the tip 450 of the faceted nozzle 410 may be formed around the aperture 412 and engage with the end of the second portion 248 of the end portion 145.

Figure 18A:
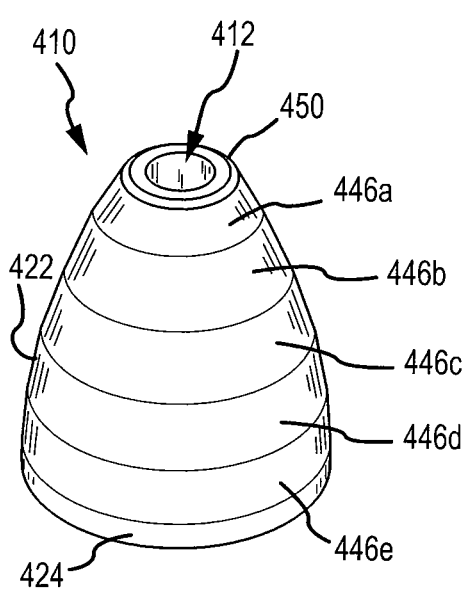
FIG. 18A is a top perspective isometric view of the nozzle of FIG. 2 removed from the powered irrigator.
Figure 18B:
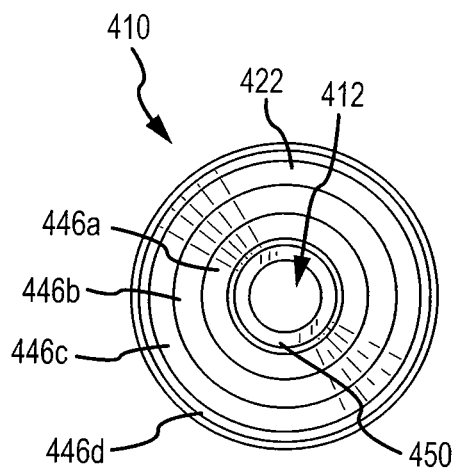
FIG. 18B is a top plan view of the nozzle illustrated in FIG. 18A.
Figure 18C:
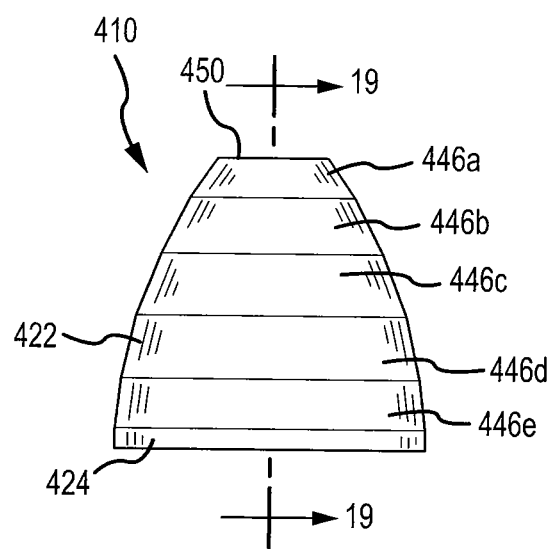
FIG. 18C is a side elevation view of the nozzle illustrated in FIG. 18A.
Figure 18D:
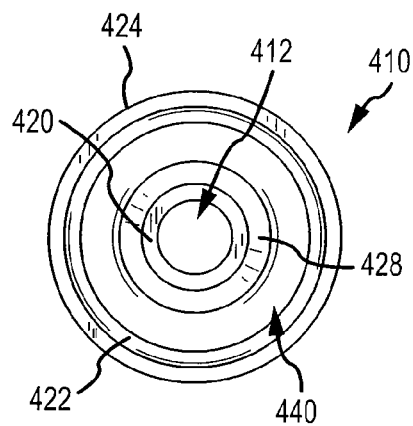
FIG. 18D is a bottom plan view of the nozzle illustrated in FIG. 18A.
Figure 18E:
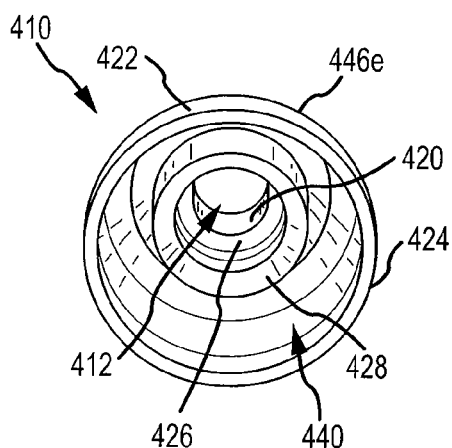
FIG. 18E is a bottom isometric view of the nozzle illustrated in FIG. 18A.
Figure 19:
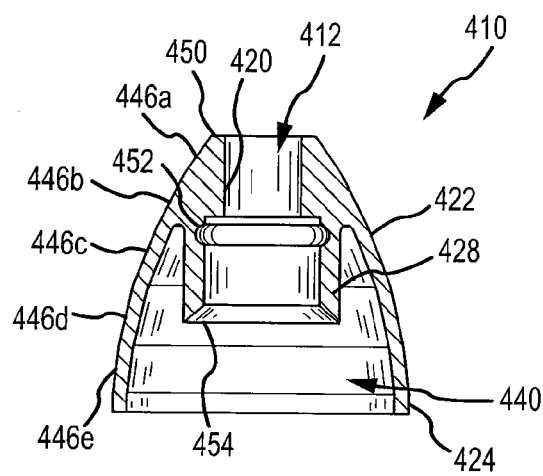
FIG. 19 is a section of the nozzle illustrated in FIG. 18A, viewed along line 19-19 in FIG. 18B.

FIG. 18A is a top isometric view of the faceted nozzle 410; FIG. 18B is a top plan view of the faceted nozzle 410; FIG. 18C is a side elevation view of the faceted nozzle 410; FIG. 18D is a bottom plan view of the faceted nozzle 410; FIG. 18E is a bottom isometric view of the faceted nozzle 410; and FIG. 19 is a cross-section view of the faceted nozzle 410, as indicated by line 19-19 in FIG. 18C. Referring to FIGS. 18A-19, the faceted nozzle 410 is self-sealing and is made of a soft elastomeric material, such as food grade silicone rubber. The nozzle 410 includes a tip 450 or apex which is the first portion of the nozzle 410 to enter the user's nostril when attached to the irrigator 100. At a center portion of the tip 450 is an outlet aperture 412.

A skirt 422 or body is formed by a wall extending downwardly and away from the tip 450, as can be see from FIG. 18A, the skirt 422 is faceted or stepped circumferentially, or otherwise made up of regions having flat extensions or mixed flat and curved extensions, as the skirt 422 extends downwards. In some implementations the skirt 422 may have a wall thickness of approximately 0.040 inches.

The skirt 422 of the faceted nozzle 410 acts to form a seal with the user's nostril when the faceted nozzle 410 is attached to the irrigator 100. The skirt 422 includes steps 446a-446e, which create ridges on the outer surface of the skirt 422. In some implementations the steps 446a-446e may be approximately the same height; however each step 446a-446e may have a different average or center diameter. In these implementations, each step 446a-446e increases the overall outer diameter of the skirt 422 and the faceted nozzle 410 maintains a generally rounded shape. For example, the first step 446a has a smaller average diameter than the second step 446b, and so on. In other implementations the steps 446a-446e may have different widths, such that the first step 446a may cover a greater portion of the outer surface of the skirt 422 than the second step 446b.

For example, as can been seen in FIG. 18A, the steps 446a-446e may be a series of stacked frustums having different outer wall angles. Each step 446a-446e is sloped at a predetermined angled and the outer wall has a larger diameter at the bottom edge of the steps 446a-446e than at the top edge of each step 446a-446e. In these implementations, each step 446a-446e decreases in diameter from the bottom edge to the top edge. Additionally, each step 446a-446e may have a different average diameter than the preceding step 446a-446e; this is because each step 446a-446e may have a different outer wall angle than the previous step 446a-446e. In some embodiments, the configuration of stacked frustum sections on top of one another may include ridges between each of the steps 446a-446e at the point of transition, from one step 446a-446e to the next; this gives the skirt 422 a faceted appearance and feel.

In these implementations, the user inserts the tip 450 into a user's nostril and then actuates the irrigator 100, allowing the solution to travel from the main body 110 to the end portion 145. Once the nasal solution enters the end portion 145, the solution enters the inner collar 428 proximate the tip 450 and exits into the nasal cavity via the outlet aperture 412. As the faceted nozzle 410 creates a seal between the nostril wall and the skirt 422 via the facets or steps 446a-446e, the nasal solution is deposited into the nasal cavity without substantially leaking around the faceted nozzle 410 and the user's nostril.

While the tip 450 is be inserted into a user's nostril, one of the steps 446a-446e creates a seal between the faceted nozzle 410 and the nostril walls. The particular step 446a-446e that engages the user's nostril depends upon the size of the user's nostril. For example, the larger the user's nostril the lower the step 446a-446e may be that engages the nostril wall. The steps 446a-446e create a better seal than a purely rounded nozzle, as the steps 446a-446e better conform to the nostril wall—the nostril wall is not purely oval-shaped or conical-shaped—and the steps 446a-446e better mimic the inner surface of the nostril wall. It should be noted that although five steps 446a-446e have been illustrated, any number of steps 446a-446e may be included. The number of steps 446a-446e may be altered to create a smoother or rougher skirt 422. For example, depending on the desired sealing level the number of steps 446a-446e may be increased or decreased.

The skirt 422, when positioned in the user's nasal passage, flexes inwardly into the void 440 formed as the skirt 422 extends away from the connection between the faceted nozzle 410 and the second portion 248 of the end portion 145. As the skirt 422 flexes when sealing with the user's nostril, it may do so irregularly around its circumference in order to closely match the shape of the user's nostril. This helps create an adequate seal between the user's nostril and the faceted nozzle 410 structure. When the faceted nozzle 410 is removed from the user's nostril, the elastomeric material of the skirt 422 springs back into its original shape. Additionally, the gently curving, cone-like shape of the faceted nozzle 410 from the tip 450 down to the terminal edge 424 of the skirt 422 allows for a close fit with a variety of sizes of nasal passages.

The skirt 422 terminates at a terminal edge 424. In some embodiments the terminal edge 424 may be a continuation of the steps 446a-446e and in other embodiments the terminal edge 424 may extend past the steps 446a-446e creating a shoulder, flange, or the like. In these embodiments, the faceted nozzle 410 may be substantially free-standing along the skirt 422, i.e., the skirt 422 and/or other outer surfaces of the faceted nozzle 410 may be substantially unrestricted. As can be seen from FIG. 17, the terminal edge 424 is unrestricted by the first portion 194 of the end portion 145.

It will be understood the user may rinse her nasal cavities using the irrigators 100, 300 provided herein, and may use the nozzle 124 and the faceted nozzle 410 on either irrigator 100 and 300. Accordingly, in one instance, if the user holds the irrigator 100, 300 in her right hand, the index finger can control the switch 122, with the middle and ring finger engaging the finger grips. The user then can hold the nozzle 124, 410 in line with the user's right nostril, with the irrigator 100, 300 underneath the user's nose, for easy insertion of the nozzle 124, 410 into the user's right nostril for the rinse operation. In such a position, the nozzle 124, 410 due to its position on the angled top surface 144 of the handle is angled away from the user's septum and towards a right or outer wall of the right nostril. Alternatively, the user may hold the irrigator 100, 300 in her left hand, with the index finger on the switch 122, and the middle and ring finger on the finger grips. The nozzle 124, 410 can then be positioned in line with the user's left nostril, with the main body of the irrigator 100, 300 extending down past the user's left cheek. The nozzle 124, 410 can then be positioned in the user's left nostril for the rinse operation. In this orientation, with the user bending gently over a sink, the nasal rinse solution will flow into the left nostril and out the right nostril into the sink without interference by the irrigator 100, 300 or the user's hand holding the irrigator. The main body 110, 310 has a rigid construction, and the main body 110, 310 or portions thereof may be composed of plastic or other polymers, composites, non-corrosive metals, and/or combinations thereof. Components may be molded, extruded, laser cut, or otherwise formed into the desired shape.

Accordingly, the powered irrigators of the present invention allow a user to irrigate her nasal cavity without using a gravity-fed supply vessel, which may be more comfortable. While the methods disclosed herein have been described and shown with reference to particular steps performed in a particular order, it will be understood that these steps may be combined, subdivided, or re-ordered to form an equivalent method without departing from the teachings of the present invention. Accordingly, unless specifically indicated herein, the order and grouping of the steps are not generally intended to be a limitation of the present invention.

A variety of embodiments and variations of structures and methods are disclosed herein. Where appropriate, common reference numbers were used for common structural and method features. However, unique reference numbers were sometimes used for similar or the same structural or method elements for descriptive purposes. As such, the use of common or different reference numbers for similar or the same structural or method elements is not intended to imply a similarity or difference beyond that described herein.

The references herein to "up" or "top", "bottom" or "down", "lateral" or "side", and "horizontal" and "vertical", as well as any other relative position descriptor are given by way of example for the particular embodiment described and not as a requirement or limitation of the powered irrigator or the apparatus and method for assembling the powered irrigator. Reference herein to "is", "are", "should", "would", or other words implying a directive or positive requirement are intended to be inclusive of the permissive use, such as "may", "might", "could" unless specifically indicated otherwise.

The apparatus and associated method in accordance with the present invention has been described with reference to particular embodiments thereof. Therefore, the above description is by way of illustration and not by way of limitation. Accordingly, it is intended that all such alterations and variations and modifications of the embodiments are within the scope of the present invention as defined by the appended claims.

What is claimed is:

1. A sinus irrigator comprising:
   a handle portion including
      a rim including at least two slots defined within a portion of the rim;
   an outlet nozzle extending from a top end of the handle;
   a pump mechanism operably coupled to a power source and received within the handle portion; and
   a reservoir operably connected to the handle portion, the reservoir including
      a generally cylindrical body defining a cavity; and
      at least two tabs operably connected to the cylindrical body and extending inwards from the cylindrical body towards the cavity; wherein
      the at least two tabs operably connect the reservoir to the handle portion to releasably secure the reservoir to the handle portion;
   rotating the reservoir in a first direction relative to the rim engages the at least two tabs with the at least two slots; and rotating the reservoir in a second direction relative to the rim disengages the at least two tabs from the at least two slots.

2. The sinus irrigator of claim 1, further comprising a fluid supply tube extending from the handle portion to the reservoir, wherein the fluid supply tube fluidly connects the reservoir with the outlet nozzle.

3. The sinus irrigator of claim 2, wherein the fluid supply tube extends through the rim to span between the handle portion and the reservoir.

4. The sinus irrigator of claim 1, further comprising a fluid supply tube operably connected to the handle portion and configured to fluidly connect the reservoir to the outlet nozzle.

5. The sinus irrigator of claim 4, wherein the handle portion further comprises a tubular fitting operably connected between the outlet nozzle and the fluid supply tube and configured to fluidly connect the outlet nozzle to the fluid supply tube.

6. The sinus irrigator of claim 1, wherein the at least two tabs extend inwards towards the cavity from an upper edge of the cylindrical body.

7. The sinus irrigator of claim 1, wherein when the handle portion is operably connected to the reservoir, an outer wall of the handle portion substantially adjacent the connection location is substantially flush with an outer wall of the reservoir portion substantially adjacent the connection location.

8. A powered sinus irrigator comprising:
a handle portion;
an outlet nozzle operably connected to the handle portion;
a pump received within the handle portion; and
a reservoir operably connected to the handle portion, the reservoir including
    a generally cylindrical body defining a cavity; and
    at least two tabs operably connected to the cylindrical body and extending inwards from the cylindrical body towards the cavity;
an intermediate member positioned between the handle portion and the reservoir, the intermediate member includes at least two slots for receiving the at least two tabs; wherein
the pump pumps fluid from the reservoir to the outlet nozzle;
the at least two tabs are slidably received within a respective one of the at least two slots to operably connect the reservoir to the handle portion to releasably secure the reservoir to the handle portion;
rotating the reservoir in a first direction relative to the handle portion engages the at least two tabs with the at least two slots; and
rotating the reservoir in a second direction relative to the handle portion disengages the at least two tabs from the at least two slots.

9. The powered sinus irrigator of claim 8, further comprising a fluid supply tube extending from the handle portion to the reservoir, wherein the fluid supply tube fluidly connects the reservoir with the outlet nozzle.

10. The sinus irrigator of claim 9, wherein the fluid supply tube extends through the intermediate member to fluidly connect to the reservoir.

11. The powered sinus irrigator of claim 8, further comprising a fluid supply tube operably connected to the handle portion and configured to fluidly connect the reservoir to the outlet nozzle.

12. The powered sinus irrigator of claim 11, wherein the handle portion further comprises a tubular fitting operably connected between the outlet nozzle and the fluid supply tube and configured to fluidly connect the outlet nozzle to the fluid supply tube.

13. The powered sinus irrigator of claim 8, wherein the intermediate member extends from a bottom end of the handle portion.

* * * * *